US007129373B2

(12) United States Patent
Coleman et al.

(10) Patent No.: US 7,129,373 B2
(45) Date of Patent: Oct. 31, 2006

(54) OXIDATION CATALYST AND PROCESS

(75) Inventors: James P. Coleman, Maryland Heights, MO (US); Martin P. McGrath, Webster Groves, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 10/366,947

(22) Filed: Feb. 14, 2003

(65) Prior Publication Data

US 2004/0010160 A1   Jan. 15, 2004

Related U.S. Application Data

(60) Provisional application No. 60/356,916, filed on Feb. 14, 2002.

(51) Int. Cl.
C07F 9/38     (2006.01)
C07F 9/40     (2006.01)

(52) U.S. Cl. .......................... 562/17; 558/145; 558/169

(58) Field of Classification Search .................. 562/17; 558/145, 169
See application file for complete search history.

(56) References Cited

U.S. PATENT DOCUMENTS

| | | | |
|---|---|---|---|
| 2,384,817 | A | 9/1945 | Chitwood |
| 3,799,758 | A | 3/1974 | Franz |
| 3,871,998 | A | 3/1975 | Rase et al. |
| 3,950,402 | A | 4/1976 | Franz |
| 3,969,398 | A | 7/1976 | Hershman |
| 4,325,843 | A | 4/1982 | Slaugh et al. |
| 4,326,992 | A | 4/1982 | Slaugh et al. |
| 4,333,916 | A | 6/1982 | Iwai et al. |
| 4,345,038 | A | 8/1982 | McCandlish et al. |
| 4,476,102 | A | 10/1984 | McCandlish et al. |
| 4,522,708 | A | 6/1985 | Leclercq et al. |
| 4,579,689 | A | 4/1986 | Hershman et al. |
| 4,582,650 | A | 4/1986 | Felthouse |
| 4,624,937 | A | 11/1986 | Chou |
| 4,696,772 | A | 9/1987 | Chou |
| 4,775,498 | A | 10/1988 | Gentilcore |
| 4,782,183 | A | 11/1988 | Goto et al. |
| 5,179,228 | A | 1/1993 | Ramon et al. |
| 5,292,936 | A | 3/1994 | Franczyk |
| 5,338,716 | A | 8/1994 | Triplett et al. |
| 5,367,112 | A | 11/1994 | Franczyk |
| 5,372,981 | A | 12/1994 | Witherspoon |
| 5,427,761 | A | 6/1995 | Grindatto et al. |
| 5,606,107 | A | 2/1997 | Smith |
| 5,627,125 | A | 5/1997 | Ebner et al. |
| 5,739,390 | A | 4/1998 | Franczyk et al. |
| 5,989,648 | A | 11/1999 | Phillips |
| 6,005,140 | A * | 12/1999 | Morgenstern et al. ........ 562/17 |
| 6,376,708 | B1 | 4/2002 | Morgenstern et al. |
| 6,417,133 | B1 | 7/2002 | Ebner et al. |
| 6,436,816 | B1 | 8/2002 | Lee et al. |
| 6,689,711 | B1 | 2/2004 | Lefebvre |
| 6,764,874 | B1 | 7/2004 | Zhang et al. |
| 2002/0068836 | A1 | 6/2002 | Haupfear et al. |
| 2002/0121460 | A1 | 9/2002 | Moy et al. |
| 2003/0228972 | A1 | 12/2003 | Birss et al. |

FOREIGN PATENT DOCUMENTS

| | | |
|---|---|---|
| EP | 1 236 509 A1 | 9/2002 |
| FR | 2 798 079 A1 | 3/2001 |
| FR | 2 798 135 A1 | 3/2001 |
| WO | WO 95/32150 A1 | 11/1995 |
| WO | WO 00/62926 A1 | 10/2000 |
| WO | WO 01/28679 A1 | 4/2001 |

OTHER PUBLICATIONS

Bouwkamp-Wijnoltz, A.L., et al., Electrochemical Reduction of Oxygen: An Alternative Method to Prepare Active $CoN_4$ Catalysts, *Electrochimica Acta.*, 1999, pp. 379-386, vol. 45.

Bouwkamp-Wijnoltz, A.L., et al., On Active-Site Heterogeneity in Pyrolyzed Carbon-Supported Iron Porphyrin Catalysts for the Electrochemical Reduction of Oxygen: An In Situ Mossbauer Study, *J. Phys. Chem.*, 2002, pp. 12993-13001, vol. 106, No. 50.

Cote, R., et al., Non-Noble Metal-Based Catalysts for the Reduction of Oxygen in Polymer Electrolyte Fuel Cells, *Journal of New Materials for Electrochemical Systems I*, 1998, pp. 7-16.

Deng, Charles Z., et al., Sputtered Cobalt-Carbon-Nitrogen Thin Films as Oxygen Reduction Electrocatalysts, *J. Electrochem. Soc.*, Oct. 1998, pp. 3507-3512, vol. 145, No. 10.

Faubert, G., et al., Iron Catalysts Prepared by High- Temperature Pyrolysis of Tetraphenylporphyrins Absorbed on Carbon Black for Oxygen Reduction in Polymer Electrolyte Fuel Cells, *Electrochimica Acta.*, 1998, pp. 341-353, vol. 43 Nos. 3-4, Great Britain.

Faubert, G., et al., Activation and Characterization of Fe-Based Catalysts for the Reduction of Oxygen in Polymer Electrolyte Fuel Cells, *Electrochimica Acta.*, 1998, pp. 1969-1984, vol. 43, Nos. 14-15, Great Britain.

Fournier, Joel, et al., Activation of Various Fe-Based Precursors on Carbon Black and Graphite Supports to Obtain Catalysts for the Reduction of Oxygen in Fuel Cells, *J. Electrochem. Soc.*, Jan. 1997, pp. 218-226, vol. 144, No. 1.

Gupta, S., et al., Methanol-Tolerant Electrocatalysts for Oxygen Reduction in a Polymer Electrolyte Membrane Fuel Cell, *J. Appl. Electrochem.*, 1998, pp. 673-682, vol. 28, No. 7.

(Continued)

*Primary Examiner*—Kamal A. Saeed
*Assistant Examiner*—Robert Shiao
(74) *Attorney, Agent, or Firm*—Senniger Powers; Joseph A. Schaper

(57) ABSTRACT

An oxidation catalyst is prepared by pyrolyzing a source of iron and a source of nitrogen on a carbon support. Preferably, a noble metal is deposited over the modified support which comprises iron and nitrogen bound to the carbon support. The catalyst is effective for oxidation reactions such as the oxidative cleavage of tertiary amines to produce secondary amines, especially the oxidation of N-(phosphonomethyl)iminodiacetic acid to N-(phosphonomethyl)glycine.

92 Claims, 12 Drawing Sheets

OTHER PUBLICATIONS

Hirai, Toshiro, et al., The Influence of Catalyst-Supporting Methods on Electrochemical Activity and the Resultant Stability of Air Electrodes Activated with Iron Pythalocyanine, *Journal of Applied Electrochemistry*, 1985, pp. 441-445, Chapman and Hall Ltd.

Lalande, G. et al., Is Nitrogen Important in the Formulation of Fe-Based Catalysts for Oxygen Reduction in Solid Polymer Fuel Cells?, *Electrochimica Acta.*, 1997, pp. 1379-1388, vol. 42, No. 9, Great Britain.

Lefevre, M., et al., Molecular Oxygen Reduction in PEM Fuel Cells: Evidence for the Simultaneous Presence of Two Active Sites in Fe-Based Catalysts, *J. Phys. Chem.*, 2002, pp. 8705-8713, vol. 106, No. 34.

Lin, W.-F., et al., On-Line FTIR Spectroscopic Investigations of Methanol Oxidation in a Direct Methanol Fuel Cell, *J. Electrochem. Soc.*, Jun. 1997, pp. 1917-1922, vol. 144, No. 6.

Markusse, A.P., et al., Platinum Deactivation: *in situ* EXAFS During Aqueous Alcohol Oxidation Reaction, *Catalysts Letters*, 1998, pp. 141-145.

Mukerjee, Sanjeev, et al., An In Situ X-Ray Absorption Spectroscopy Investigation of the Effect of Sn Additions to Carbon-Supported Pt Electrocatalysts, *Journal of The Electrochemical Society*, 1999, pp. 600-606, vol. 146, No. 2.

Okada, Tatsuhiro, et al., Oxygen Reduction Characteristics of Heat-Treated Catalysts Based on Cobalt-Porphyrin Ion Complexes, *J. Electrochem. Soc.*, Mar. 1998, pp. 815-822, vol. 145, No. 3.

Toda, Takako, et al., Enhancement of the Electroreduction of Oxygen on Pt Alloys with Fe, Ni, and Co, *Journal of The Electrochemical Society*, 1999, pp. 3750-3756, vol. 146, No. 10.

Torrens, Manuel A., Mossbauer Studies on Oxo-Bridged Iron (III) Porphines, *Journal of the American Chemical Society*, Jun. 14, 1972, pp. 4160-4162, vol. 94, No. 12.

Bett, J.S., et al., Platinum-macrocycle Co-catalysts for the Electrochemical Oxidation of Methanol, *Electrochimica Acta*, 1998, pp. 3645-3655, vol. 43, No. 24, Elsevier Science Ltd., Great Britain.

Faubert, G., et al., Oxygen Reduction Catalysts for Polymer Electrolyte Fuel Cells from the Pyrolysis of Fe Acetate Absorbed on 3,4,9,10-Perylenetetracarboxylic Dianhydride, *Electrochimica Acta*, 1999, pp. 2589-2603, vol. 44, Elsevier Science Ltd., Great Britain.

Okada, T., et al., Oxygen Reduction Characteristics of Graphite Electrodes Modified with Cobalt Di-Quinolyldiamine Derivatives, *Electrochimica Acta*, 2000, pp. 4419-4428, vol. 45, Elsevier Science Ltd., Great Britain.

International Search Report from the European Patent Office dated Jun. 30, 2003.

He, P., et al., "Oxygen Reduction Catalysts For Polymer Electrolyte Fuel Cells From the Pyrolysis of Various Transition Metal Acetates Adsorbed on 3, 4, 9, 10-Perylenetetracarboxylic Dianhydride," *Journal of New Material for Electrochemical Systems*, 1999, pp. 243-251, vol. 2, Journal of New Material Electrochemical Systems.

Lefévre, M., et al., "$O_2$ Reduction in PEM Fuel Cells: Activity and Active Site Structural Information for Catalysts Obtained by the Pyrolysis at High Temperature of Fe Precursors," *Journal of Physical Chemistry B*, 2000, pp. 11238-11247, vol. 104, American Chemical Society.

Levy, R. B., et al., "Platinum-Like Behavior of Tungsten Carbide in Surface Catalysis," *Science*, 1973, pp. 547-549, vol. 181.

Oyama, S. T., "Preparation and Catalytic Properties of Transition Metal Carbides and Nitrides," *Catalysis Today*, 1992, pp. 179-200, vol. 15, Elsevier Science Publishers B. V., Amsterdam.

Wang, H., et al., "Effect of the Pre-Treatment of Carbon Black Supports on the Activity of Fe-Based Electocatalysts for the Reduction of Oxygen," *Journal of Physical Chemistry B*, 1999, pp. 2042-2049, vol. 103, American Chemical Society.

Liang, C., et al., "Activated Carbon Supported Bimetallic CoMo Carbides Synthesized by Carbothermal Hydrogen Reduction," *Carbon*, 2003, pp. 1833-1839, vol. 41, Elsevier Science.

Pinel, Catherine, et al., "Effect of the Nature of Carbon Catalysts on Glyphosate Synthesis", *Academic Press*, 1999, pp. 515-519.

Alvarez-Merino, M. et al., "Tungsten Catalysts Supported on Activated Carbon," *Journal of Catalysis*, 2000, pp. 363-373, vol. 192, Academic Press.

Bridgewater, A. J., et al., "Reactions of Carbon Monoxide with Hydrogen Over Molybdenum/Charcoal Catalysts," *Journal of Catalysis*, 1982 pp. 116-125, vol. 78.

Dandekar, A., et al., "Carbon-Supported Copper Catalysts," *Journal of Catalysis*, 1999, pp. 131-154, vol. 183, Academic Press.

Franz, J. E., et al., Glyphosate: A Unique Global Herbicide, Chapter 8-"Methods of Preparing Glyphosate," *American Chemical Society*, 1997 pp. 233-262, Washington D.C.

Granger, P., et al., "Kinetics of the NO and CO Reaction Over Platinum Catalysts," *Journal of Catalysis*, 1998, pp. 304-314, Academic Press.

Kimbara, N., et al., "New Type of TiN Support For Hydroprocessing Catalyst Yst.," *Catal. Lett.*, 1990, pp. 3-6, vol. 6.

Lin, C. A., et al., "Characterization of Boron-Nitride-Supported Pt Catalysts for the Deep Oxidation of Benzene," *Journal of Catalysis*, 2002, pp. 39-45, vol. 210, Elsevier Science, USA.

Mordenti, D., et al., "New Synthesis of $Mo_2$ 14 nm in Average Size Supported on a High Specific Surface Area Carbon Material," *Journal of Solid State Chemistry*, 1998, pp. 114-120, vol. 141, Academic Press.

Murav'ev, V. I., "Carbonitriding In A Fluidized Bed of Carbon-Graphite Materials," *Metal Science and Heat Treatment*, 1976, pp. 492-495, vol. 18, No. 5-6, Consultants Bureau, New York.

Nagai, M., et al., "Catalytic Activity and Surface Properties of Nitride Molybdena-Alumina for Carbazole Hydrodenitrogenation," *Journal of Catalysis*, 2000, pp. 128-137, vol. 191, Academic Press.

Nhut, J.M., et al., "Synthesis and Catalytic Uses of Carbon and Silicon Carbide Nanostructures," *Catalysis Today*, 2002, pp. 11-32, vol. 76, Elsevier Science B.V.

Oyama, S. T., et al., "Preparation and Characterization of Early Transition-Metal Carbides and Nitrides," *Industrial & Engineering Chemistry Research*, 1988, pp. 1639-1648, vol. 27, No. 9, American Chemial Society.

Sedunov, V. K., et al., "Structure and Phase Composition of Surface Zones of Carburized and Carbonitrided Layers," *Metal Science and Heat Treatment*, 1977, pp. 742-745, vol. 19, Nos. 9-10, Consultants Bureau, New York.

Van Veen, J. A. R., et al., "On the Effect of a Heat Treatment on the Structure of Carbon-Supported Metalloporphyrins and Phthalocyanines", *Electrochimica Acta*, 1988, pp. 801-804, vol. 33, No. 6, Pergamon Press plc., Great Britain.

Van Veen, J. A. Rob, et al., "Effect of Heat Treatment on the Performance of Carbon-supported Transition-metal Chelates in the Electrochemical Reduction of Oxygen", *J. Chem Soc., Faraday Trans. 1*, 1981, pp. 2827-2843, vol. 77, The Royal Society of Chemistry, United Kingdom.

Alves, M.C. Martin, et al., "Characterization of New Systems for the Catalytic Electroreduction of Oxygen by Electrochemistry and X-Ray Absorption Spectroscopy," *NATO ASI Series, Series C: Mathematical and Physical Sciences, Synchrotron Techniques in Interfacial Electrochemistry*, 1994, pp. 281-293, vol. 432, Kluwer Academic Press, The Netherlands.

Birss, V. I., et al., "Non-Noble Metal Catalysts for PEM Oxygen Reduction Based on Sol Gel Derived Cobalt Nigrogen Compounds," *Electrochemical Society Proceedings*, 2002, pp. 89-98, vol. 2002-31, Electrochemical Society.

Collman, James P., et al., "Electrode Catalysis of the Four-Electron Reduction of Oxygen to Water by Dicobalt Face to Face Porphyrins," *Journal of American Chemical Society*, 1980, pp. 6027-6036, vol. 102, American Chemical Society.

Dignard-Bailey, L. et al., "Graphitization and Particle Size Analysis of Pyrolyzed Cobalt Phthalocyanine/Carbon Catalysts for Oxygen Reduction in Fuel Cells," *Journal of Materials Research*, 1994, pp. 3203-3209, vol. 9, No. 12, Materials Research Society.

Durand, Richard R., et al., "Catalysis of Dioxygen Reduction at Graphite Electrodes by an Adsorbed Cobalt(II) Porphyrin," *Journal of Electroanalytical Chemistry*, 1982, pp. 273-289, vol. 134, No. 2, Elsevier Sequoia S.A., Lausanne, The Netherlands.

Ewen, Richard J., et al., "X-Ray Photoelectron Spectroscopy of Clean and Gas-Doped Films of Phthalocyanines," *Journal of Phys-*

*ics Condensed Matter*, 1991, vol.3 pp. S303-S310, IOP Publishing Ltd., An Institute of Physics Journal, United Kingdom.

Faubert, G. et al., "Heat-Treated Iron and Cobalt Tetraphenylporphyrins Adsorbed on Carbon Black: Physical Characterization and Catalytic Properties of these Materials For the Reduction of Oxygen in Polymer Electrolyte Fuel Cells," *Electrochimica Acta*, 1996, pp. 1689-1701, vol. 41, No. 10, Elsevier Science Ltd., Great Britain.

Jasinski, Raymond, "Cobalt Phthalocyanine as a Fuel Cell Cathode," *Journal of the Electrochemical Society*, 1965, pp. 526-528, vol. 112, No. 5.

Kim, Do-Woan, et al., "CoMo Bimetallic Nitride Catalysts for Thiophene HDS," *Catalysis Letters*, 1997, pp. 91-95, vol. 43, Nos. 1-2, J.C. Baltzer AG, Science Publishers.

Lalande, G., et al., "Rotating Disk Electrode Measurements on the Electrocatalytic Activity of Heat-Treated Carbon Supported Cobalt Phthalocyanine Catalysts for Oxygen Reduction," *Electrochemical Society Proceedings*, 1994, pp. 418-429, Electrochemical Society.

Lalande, G., et al., "Catalytic Activity and Stability of Heat-Treated Iron Phthalocyanines for the Electroreduction of Oxygen in Polymer Electrolyte Fuel Cells," *Journal of Power Sources*, 1996, pp. 227-237, vol. 61, Elsevier Science S.A.

Lalande, G., et al., "Chromium-Based Electrocatalysts for Oxygen Reduction in Polymer Electrolyte Fuel Cells," *New Materials for Fuel Cell and Modern Battery Systems II, Proceedings of the International Symposium on New Materials for Fuel Cell and Modern Battery Systems, 2nd Montreal*, Jul. 6-10, 1997, pp. 768-777, Ecole Polytechnique De Montreal, Monteal Que.

Lalande, G., et al., "Electroreduction of Oxygen in Polymer Electrolyte Fuel Cells by Activated Carbon Coated Cobalt Nanocyrstallites Produced by Electric Arc Discharge," *Chemistry of Materials*, 1997, pp. 784-790, vol. 9, No. 3, American Chemical Society.

Lefevre, M., et al., "Functionalities of a Fe-Based Catalyst Evidence of ToF-SIMS in Relation with the Electroreduction of Oxygen in Polymer Electrolyte Fuel Cells," *Secondary Ion Mass Spectrometry, SIMS XII, Proceedings of the International Conference on Secondary Ion Mass Spectrometry*, 1999, pp. 447-450, Elsevier Science, Amsterdam, Netherlands.

Milad, Issa K., et al., "A Comparison of Bulk Metal Nitride Catalysts for Pyridine Hydrodenitrogenation," *Catalysis Letters*, 1998, pp. 113-119, vol. 52, No. 1-2, J.C. Baltzer AG Science Publishers.

Nishihara, Hiroshi, et al., "Electrochemical Olefin Epoxidation with Manganese meso-Tetraphenylporphyrin Catalyst and Hydrogen Peroxide Generation at Polymer-Coated Electrodes," *Inorganic Chemistry*, 1990, pp. 1000-1006, vol. 29, No. 5, American Chemical Society.

Ohta, R., et al., "Origin of N 1s Spectrum in Amorphous Carbon Nitride Obtained by X-Ray Photoelectron Spectroscopy," *Thin Solid Films*, 2003, pp. 296-302, vol. 434, Elsevier.

Singh, A., et al., "X-Ray Photoelectron Spectroscopy of Nitrogen-Implanted Cemented Tungsten Carbide (WC-Co)," *Journal of Materials Science Letters*, 1990, pp. 1101-1102, vol. 9, Chapman and Hall Ltd.

Takano, I., et al., "Nitrogenation of Various Transition Metals By $N_2+$-Ion Implantation," *Applied Surface Science*, 1989, pp. 25-32, vol. 37, Elsevier Science Publishers B.V., North-Holland, Amsterdam.

Van Der Putten, A., et al., "Oxygen Reduction on Pyrolysed Carbon-Supported Transition Metal Chelates," *Journal of Electroanalytical Chemistry and Interfacial Electrochemistry*, 1986, pp. 233-244, vol. 205, Elsevier Sequoia S.A. Lausanne, The Netherlands.

Weng, L.T., et al., "Characterization of Electrocatalysts for Oxygen Reduction by TOF SIMS," *Secondary Ion Mass Spectrometry, Proceedings of the International Confernece on Secondary Ion Mass Spectrometry, 9th, Yokohama*, Nov. 7-12, 1994, pp. 442-445, Wiley, Chichester, United Kingdom.

Weng, L.T., et al., "Surface Characterization by Time-of-Flight SIMS of a Catalyst for Oxygen Electroreduction: Pyrolyzed Cobalt Phthalocyanine-On-Carbon Black," *Applied Surface Science*, 1995, pp. 9-21, vol. 84, Elsevier Science B.V.

US 6,337,298, 01/2002, Ebner et al. (withdrawn)

* cited by examiner

OXIDATION CATALYST AND PROCESS

CROSS-REFERENCE TO RELATED APPLICATIONS

This application claims the benefit of U.S. Provisional Application Ser. No. 60/356,916, filed Feb. 14, 2002, the entire text of which is hereby incorporated herein by reference.

BACKGROUND OF THE INVENTION

This invention is directed to redox reaction catalysts, and more particularly to improved catalysts effective for the reduction of molecular oxygen in the conduct of oxidation reactions. The invention more particularly relates to the preparation of secondary amines by catalytic oxidative cleavage of tertiary amines, e.g., the preparation of N-(phosphonomethyl)glycine by catalytic oxidation of N-(phosphonomethyl)iminodiacetic acid.

N-(phosphonomethyl)glycine (known in the agricultural chemical industry as "glyphosate") is described in Franz, U.S. Pat. No. 3,799,758. N-(phosphonomethyl)glycine and its salts are conveniently applied as a post-emergent herbicide in an aqueous formulation. It is a highly effective and commercially important broad-spectrum herbicide useful in killing or controlling the growth of a wide variety of plants, including germinating seeds, emerging seedlings, maturing and established woody and herbaceous vegetation, and aquatic plants.

Various methods for making N-(phosphonomethyl)glycine are known in the art. Franz, U.S. Pat. No. 3,950,402, teaches that N-(phosphonomethyl)glycine may be prepared by the liquid phase oxidative cleavage of N-(phosphonomethyl)iminodiacetic acid (sometimes referred to as "PMIDA") with oxygen in the presence of a catalyst comprising a noble metal deposited on the surface of an activated carbon support:

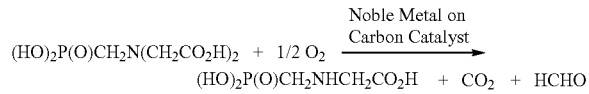

Other by-products also may form, such as formic acid, which is formed by the oxidation of the formaldehyde by-product; and aminomethylphosphonic acid, which is formed by the oxidation of N-(phosphonomethyl)glycine. Even though the Franz method produces an acceptable yield and purity of N-(phosphonomethyl)glycine, high losses of the costly noble metal into the reaction solution (i.e., "leaching") result because under the oxidation conditions of the reaction, some of the noble metal is oxidized into a more soluble form and both N-(phosphonomethyl)iminodiacetic acid and N-(phosphonomethyl)glycine act as ligands which solubilize the noble metal.

In U.S. Pat. No. 3,969,398, Hershman teaches that activated carbon alone, without the presence of a noble metal, may be used to effect the oxidative cleavage of N-(phosphonomethyl)iminodiacetic acid to form N-(phosphonomethyl) glycine. In U.S. Pat. No. 4,624,937, Chou further teaches that the activity of the carbon catalyst taught by Hershman may be increased by removing the oxides from the surface of the carbon catalyst before using it in the oxidation reaction. See also, U.S. Pat. No. 4,696,772, which provides a separate discussion by Chou regarding increasing the activity of the carbon catalyst by removing oxides from the surface of the carbon catalyst. Although these processes obviously do not suffer from noble metal leaching, they do tend to produce greater concentrations of formaldehyde by-product when used to effect the oxidative cleavage of N-(phosphonomethyl)iminodiacetic acid. This formaldehyde by-product is undesirable because it reacts with N-(phosphonomethyl)glycine to produce unwanted by-products (mainly N-methyl-N-(phosphonomethyl)glycine, sometimes referred to as "NMG") which reduce the N-(phosphonomethyl)glycine yield. In addition, the formaldehyde by-product itself is undesirable because of its potential toxicity. See Smith, U.S. Pat. No. 5,606,107.

Optimally, therefore, it has been suggested that the formaldehyde be simultaneously oxidized to carbon dioxide and water as the N-(phosphonomethyl)iminodiacetic acid is oxidized to N-(phosphonomethyl)glycine in a single reactor, thus giving the following reaction:

As the above teachings suggest, such a process requires the presence of both carbon (which primarily effects the oxidation of N-(phosphonomethyl)iminodiacetic acid to form N-(phosphonomethyl)glycine and formaldehyde) and a noble metal (which primarily effects the oxidation of formaldehyde to form carbon dioxide and water). Like Franz, Ramon et al. (U.S. Pat. No. 5,179,228) teach using a noble metal deposited on the surface of a carbon support. To reduce the problem of leaching (which Ramon et al. report to be as great as 30% noble metal loss per cycle), however, Ramon et al. teach flushing the reaction mixture with nitrogen under pressure after the oxidation reaction is completed to cause re-deposition of the noble metal onto the surface of the carbon support. According to Ramon et al., nitrogen flushing reduces the noble metal loss to less than 1%.

Using a different approach, Felthouse (U.S. Pat. No. 4,582,650) teaches using two catalysts: (i) an activated carbon to effect the oxidation of N-(phosphonomethyl) iminodiacetic acid into N-(phosphonomethyl)glycine, and (ii) a co-catalyst to concurrently effect the oxidation of formaldehyde to carbon dioxide and water. The co-catalyst consists of an aluminosilicate support having a noble metal located within its pores. The pores are sized to exclude N-(phosphonomethyl)glycine and thereby prevent the noble metal of the co-catalyst from being poisoned by N-(phosphonomethyl)glycine. According to Felthouse, use of these two catalysts together allows for the simultaneous oxidation of N-(phosphonomethyl)iminodiacetic acid to N-(phosphonomethyl)glycine and of formaldehyde to carbon dioxide and water. This approach, however, suffers from several disadvantages: (1) it is difficult to recover the costly noble metal from the aluminosilicate support for re-use; (2) it is difficult to design the two catalysts so that the rates between them are matched; and (3) the carbon support, which has no noble metal deposited on its surface, tends to deactivate at a rate which can exceed 10% per cycle.

Ebner et al., in U.S. Pat. No. 6,417,133, describe a deeply reduced noble metal on carbon catalyst which is characterized by a CO desorption of less than 1.2 mmole/g, preferably less than 0.5 mmole/g, when a dry sample of the catalyst, after being heated at a temperature of about 500° C. for about 1 hour in a hydrogen atmosphere and before being exposed to an oxidant following the heating in the hydrogen atmosphere, is heated in a helium atmosphere from about 20° to about 900° C. at a rate of about 10° C. per minute, and then at about 900° C. for about 30 minutes. The catalyst is further characterized as having a ratio of carbon atoms to oxygen atoms of at least about 20:1, preferably at least about 30:1, at the surface as measured by x-ray photoelectron spectroscopy after the catalyst is heated at a temperature of about 500° C. for about 1 hour in a hydrogen atmosphere and before the catalyst is exposed to an oxidant following the heating in the hydrogen atmosphere.

The catalysts of U.S. Pat. No. 6,417,133 have proven to be highly advantageous and effective catalysts for the oxidation of N-(phosphonomethyl)iminodiacetic acid to N-(phosphonomethyl)glycine, and for the further oxidation of by-product formaldehyde and formic acid, and without excessive leaching of noble metal from the carbon support. It has further been discovered that these catalysts are effective in the operation of a continuous process for the production of N-(phosphonomethyl)glycine by oxidation of N-(phosphonomethyl)iminodiacetic acid.

The advent of continuous processes for the oxidation of N-(phosphonomethyl)iminodiacetic acid has created an opportunity for further improvements in productivity through the development of catalysts which accelerate the rate of oxidation of N-(phosphonomethyl)iminodiacetic acid and/or formaldehyde beyond the rates achievable with the catalysts of U.S. Pat. No. 6,417,133. Since the productivity of a continuous oxidation reactor is not constrained by the turnaround cycle of a batch reactor, any improvement in reaction kinetics translates directly into an increase in the rate of product output per unit reactor volume.

Carbon and noble metal sites on the catalysts of U.S. Pat. No. 6,417,133 are highly effective for transfer of electrons in the oxidation of N-(phosphonomethyl)iminodiacetic acid, and the noble metal sites are especially effective for this purpose in the oxidation of formaldehyde and formic acid. However, the productivity of these reactions could be enhanced if the catalyst were more effective for transfer of electrons in the concomitant reduction of molecular oxygen, which can be a rate limiting step in the overall catalytic reaction between molecular oxygen and the N-(phosphonomethyl)iminodiacetic acid, formaldehyde, and formic acid substrates.

SUMMARY OF THE INVENTION

Among the several objects of the present invention, therefore, may be noted the provision of an effective oxidation catalyst; the provision of such a catalyst which promotes reduction of molecular oxygen in the course of oxidation reactions; the provision of such a catalyst which is effective for the conversion of tertiary amines to secondary amines by oxidative cleavage; the provision of such a catalyst which is effective for the preparation of secondary amines in high productivity; the provision of such a catalyst which is effective for the oxidation of the tertiary amine, N-substituted N-(phosphonomethyl)glycine, to the secondary amine, N-(phosphonomethyl)glycine; the provision of such a catalyst which is particularly effective for the oxidation of N-(phosphonomethyl)iminodiacetic acid to N-(phosphonomethyl)glycine; the provision of such a catalyst which is effective for the preparation of N-(phosphonomethyl)glycine in high productivity; the provision of such a catalyst which is effective for the preparation of N-(phosphonomethyl)glycine in high yield based on N-(phosphonomethyl)iminodiacetic acid; and the provision of such a catalyst which is effective for the further oxidation of by-product $C_1$ compounds produced in the oxidation of N-(phosphonomethyl)iminodiacetic acid to N-(phosphonomethyl)glycine.

Further objects of the invention include the provision of a novel catalytic oxidation process for the conversion of tertiary amines to secondary amines, and more particularly, the conversion of N-(phosphonomethyl)iminodiacetic acid to N-(phosphonomethyl)glycine; and the provision of such a process which is effective for the preparation of N-(phosphonomethyl)glycine in high productivity and high yield; the provision of such a process which produces a N-(phosphonomethyl)glycine product of high quality with commercially acceptable maximum concentrations of by-products; and the provision of such a process in which $C_1$ by-products of N-(phosphonomethyl)iminodiacetic acid oxidation are also effectively oxidized.

Briefly therefore, an embodiment of the invention is directed to an oxidation catalyst comprising a noble metal deposited over a modified carbon support. The modified carbon support comprises carbon having a transition metal and nitrogen thereon, wherein the transition metal is selected from the group consisting of iron and cobalt.

Further, another embodiment of the invention is directed to a process for the preparation of a redox catalyst. The process comprises pyrolyzing a source of iron or cobalt and a source of nitrogen on a carbon support surface to provide a modified carbon support comprising iron or cobalt and nitrogen thereon. Thereafter, a noble metal is deposited on the modified carbon support.

Still further, another embodiment of the invention is directed to a process for the oxidation of an organic substrate. The process comprises contacting an organic substrate with an oxidizing agent in the presence of a oxidation catalyst comprising a noble metal deposited over a modified carbon support. The modified carbon support has a transition metal and nitrogen thereon. The transition metal is selected from the group consisting of iron and cobalt.

Still further, another embodiment of the invention is directed to a process for the oxidation of an organic substrate. The process comprises contacting an organic substrate with an oxidizing agent in the presence of a catalyst comprising a modified carbon support. The modified carbon support has a transition metal/nitrogen composition thereon and the transition metal of the catalyst is selected from the group consisting of iron and cobalt. The process is further characterized in that the catalyst comprises the transition metal/nitrogen composition in such proportion that the Fe, Co or the sum of (Fe+Co) of the transition metal/nitrogen composition constitutes at least about 0.1% by weight of the catalyst, and the nitrogen of the transition metal/nitrogen composition constitutes at least about 0.1% by weight of the catalyst.

Other features of the invention will be in part apparent and in part pointed out hereinafter.

DESCRIPTION OF THE PREFERRED EMBODIMENTS

Figure 1:
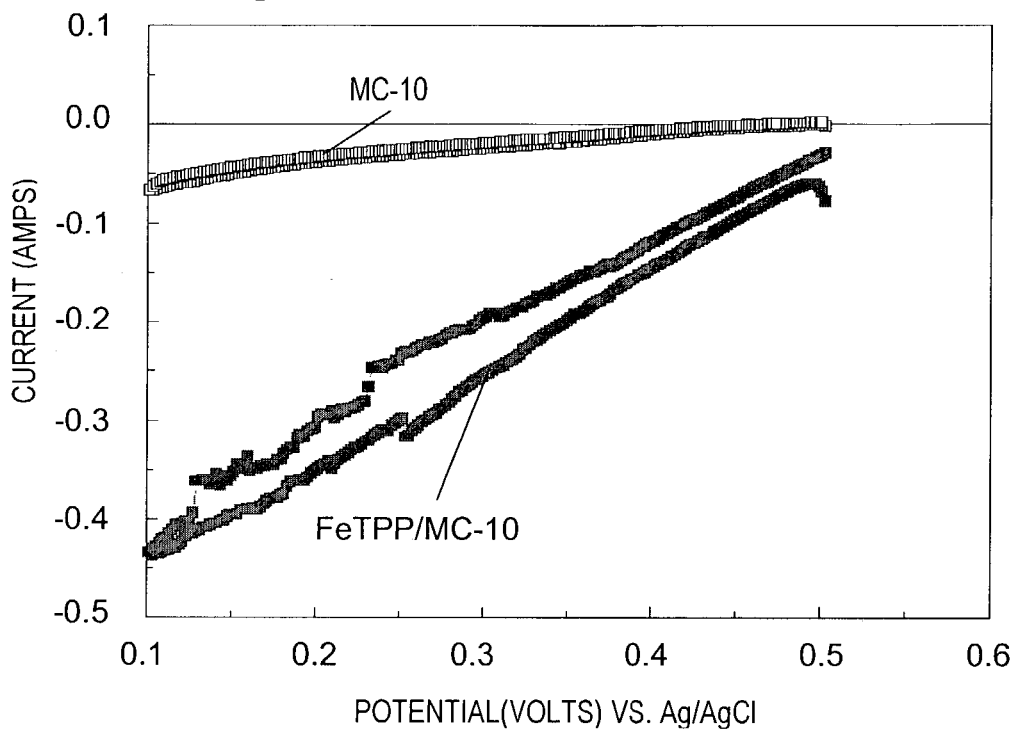
FIG. 1 shows cyclic voltammograms for the reduction of molecular oxygen as obtained in accordance with the procedure of Example 1 comparing a particulate carbon catalyst prepared in accordance with Chou, U.S. Pat. No. 4,696,772, and designated MC-10 with a particulate carbon catalyst of the invention prepared by pyrolysis of FeTPP on MC-10 and designated FeTPP/MC-10.

In accordance with the invention, it has been discovered that the oxidation of tertiary amines to secondary amines can be effectively promoted by a catalyst comprising a carbon body having bound thereto a composition comprising a transition metal and nitrogen. Such catalysts are prepared, e.g., by the pyrolysis of an Fe or Co co-ordination compound on the surface of a particulate carbon support, wherein the co-ordination ligands comprise nitrogen, more particularly, coordinated nitrogen atoms. The catalysts of the invention have been found particularly useful in oxidation reactions conducted in an aqueous reaction medium, such as the oxidation of N-(phosphonomethyl)iminodiacetic acid to N-(phosphonomethyl)glycine, especially where the catalyst further comprises a noble metal at the surface of the carbon, wherein the transition metal/nitrogen composition on carbon constitutes a modified carbon support for the noble metal. Although the present invention is not limited to or dependent on a particular theory, it is believed that the Fe/N or Co/N composition on the carbon catalyst promotes the reduction of molecular oxygen in the course of the oxidation of a substrate wherein electrons transferred from the substrate are combined with protons and molecular oxygen to ultimately form water. It further appears that the Fe/N or Co/N composition serves as an active phase which promotes the reduction of oxygen by supply of electrons removed from the substrate in the oxidation thereof.

Thus, for example, in the oxidation of methane:

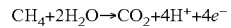

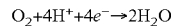

The function of the catalyst of the invention can be analogized to a short circuited fuel cell. Active Fe/N or Co/N sites on the catalyst are believed to function as efficient cathodic sites at which electrons are supplied in the reduction of molecular oxygen. Noble metal and carbon sites are believed to randomly function as either anodic sites in which electrons are transferred to the catalyst body from the substrate to be oxidized, or cathodic sites at which electrons are supplied in the reduction of oxygen. Electron transfer through the conductive carbon body between anodic and cathodic sites completes the circuit.

The catalyst of the invention has been found highly effective for the preparation of N-(phosphonomethyl)glycine by the catalytic oxidation of N-(phosphonomethyl)iminodiacetic acid with molecular oxygen. By comparison with catalysts previously available to the art, the catalyst of the invention significantly enhances rate of oxidation of N-(phosphonomethyl)iminodiacetic acid. It is also effective for oxidation of $C_1$ by-products (e.g., formaldehyde and formic acid), and enhances the reaction rate constants in these reactions as well. It thus appears that productivity of a process for the preparation of N-(phosphonomethyl)glycine can be materially enhanced by use of the catalyst of the invention. It has further been found that this catalyst can be used to produce N-(phosphonomethyl)glycine in high yield and high quality, without significant over-oxidation to aminomethylphosphonic acid or formation of N-methyl-N(phosphonomethyl)glycine.

The carbon support for the catalyst can assume a variety of forms. In one embodiment of this invention, the support is a monolithic support. Suitable monolithic supports may have numerous different shapes. A monolithic support may be, for example, in the form of a screen, a honeycomb, or in the form of a reactor impeller.

In a particularly preferred embodiment, the carbon support is in the form of particulates. Because particulate supports are especially preferred, most of the following discussion focuses on embodiments which use a particulate support. It should be recognized, however, that this invention is not limited to the use of particulate supports.

Suitable particulate supports may have a wide variety of shapes. For example, such supports may be in the form of pellets, granules and powders. These particulate supports may be used in a reactor system as free particles, or, alternatively, may be bound to a structure in the reactor system, such as a screen or an impeller. Preferably, the support is in the form of a powder. Granular supports may be preferred where the catalyst is used in a fixed bed reactor, e.g., of the type described in coassigned U.S. Publication No. US-2002-0068836-A1, which is expressly incorporated herein by reference. U.S. Publication No. US-2002-0068836-A1 is directed to continuous processes for the oxidation of N-(phosphonomethyl)iminodiacetic acid to N-(phosphonomethyl)glycine.

Typically, a support which is in particulate form comprises a broad size distribution of particles. For powders, preferably at least about 95% of the particles are from about 2 to about 300 μm in their largest dimension, more preferably at least about 98% of the particles are from about 2 to about 200 μm in their largest dimension, and most preferably about 99% of the particles are from about 2 to about 150 μm in their largest dimension with about 95% of the particles being from about 3 to about 100 μm in their largest dimension. Particles being greater than about 200 μm in their largest dimension tend to fracture into super-fine particles (i.e., less than 2 μm in their largest dimension), which are difficult to recover.

A variety of carbon supports can be used in the catalyst of the invention, including graphitic carbon. However, the specific surface area of the carbon support, measured by the Brunauer-Emmett-Teller (BET) method using $N_2$, is preferably from about 10 to about 3,000 $m^2/g$ (surface area of carbon support per gram of carbon support), more preferably from about 500 to about 2,100 $m^2/g$, and still more preferably from about 750 to about 2,100 $m^2/g$. In some embodiments, the most preferred specific area is from about 750 to about 1,750 $m^2/g$.

The pore volume of the carbon support may vary widely. Using the measurement method described in Example 1 of U.S. Pat. No. 6,417,133, the pore volume preferably is from about 0.1 to about 2.5 ml/g (pore volume per gram of catalyst), more preferably from about 0.2 to about 2.0 ml/g, and most preferably from about 0.4 to about 1.7 ml/g. Catalysts comprising supports with pore volumes greater than about 2.5 ml/g tend to fracture easily. On the other hand, catalysts comprising supports having pore volumes less than 0.1 ml/g tend to have small surface areas and therefore low activity.

Carbon supports for use in the present invention are commercially available from a number of sources. The following is a listing of some of the activated carbons which may be used with this invention: Darco G-60 Spec and Darco X (ICI-America, Wilmington, Del.); Norit SG Extra, Norit EN4, Norit EXW, Norit A, Norit Ultra-C, Norit ACX, and Norit 4×14 mesh (Amer. Norit Co., Inc., Jacksonville, Fla.); Gl-9615, VG-8408, VG-8590, NB-9377, XZ, NW, and JV (Barnebey-Cheney, Columbus, Ohio); BL Pulv., PWA Pulv., Calgon C 450, and PCB Fines (Pittsburgh Activated Carbon, Div. of Calgon Corporation, Pittsburgh, Pa.); P-100 (No. Amer. Carbon, Inc., Columbus, Ohio); Nuchar CN, Nuchar C-1000 N, Nuchar C-190 A, Nuchar C-115 A, and Nuchar SA-30 (Westvaco Corp., Carbon Department, Covington, Va.); Code 1551 (Baker and Adamson, Division of Allied Amer. Norit Co., Inc., Jacksonville, Fla.); Grade 235, Grade 337, Grade 517, and Grade 256 (Witco Chemical Corp., Activated Carbon Div., New York, N.Y.); Columbia SXAC (Union Carbide New York, N.Y.) and CP-117 (Engelhard Corp., Iselin, N.J.).

The catalysts are preferably prepared by first depositing a co-ordination compound comprising an Fe or Co salt and ligands containing nitrogen. Any of a wide variety of ligands may be used. The main requirement for the ligand is that it be subject to pyrolysis to yield nitrogen that is bound to the carbon surface to provide a transition metal/nitrogen composition which contributes to adsorption and/or reduction of molecular oxygen. It is also desirable that the ligand have an affinity, in fact preferably an appreciable solubility, in the liquid medium from which the co-ordination complex is deposited on a carbon body as described below.

Preferred ligands for the co-ordination compound comprise porphyrins or porphyrin derivatives such as tetraphenyl porphyrin. Generally, other exemplary nitrogen-containing organic ligands comprise five or six membered heterocyclic rings comprising nitrogen. Suitable ligands useful in the preparation of the catalyst include polyacrylonitrile, phthalocyanines, pyrrole, substituted pyrroles, polypyrroles, pyridine, substituted pyridines, bipyridyls (e.g., bypyridines), imidazole, substituted imadazoles, pyrimidine, substituted pyrimidines, acetonitrile, o-phenylenediamines, salen ligands, p-phenylenediamines, and cyclams. The ligands are preferably bound to an Fe or Co salt such as $FeCl_2$, $FeCl_3$, $FeSO_4$, $Fe(OAc)_3$, $CoCl_2$, $CoBr_3$, $Co_2(SO_4)_3$, Fe pentacarbonyl, dicobalt octacarbonyl, and the like. Although the oxidative state of the transition metal ion is not critical, it is believed that a co-ordination complex comprising a transition metal ion of relatively low oxidation state, e.g., $Fe^{+2}$ may be effective to reduce a species on the carbon surface, leading to a stronger bond between the metal and the surface.

To deposit the co-ordination compound on the carbon support, a suspension is prepared comprising a particulate carbon support and the co-ordination compound in a suitable medium, and preferably agitated for a time sufficient for adsorption of the co-ordination compound on the carbon surface. For example, a suspension may be prepared in an organic polar solvent such as acetone, acetonitrile, ethanol, methanol, tetrahydrofuran, methyl ethyl ketone, methyl isobutyl ketone, i-propanol, or dimethylformamide containing particulate carbon in a proportion of from about 5 to about 20 grams/L and an Fe co-ordination compound such as an 5,10,15,20-tetraphenyl-21H,23H-porphine iron (III) halide in a proportion of from about 1 to about 10 grams/L, with the carbon and iron co-ordination complex in such relative proportions that the weight ratio of Fe/C is in the range of from about 0.001 to about 0.1, preferably from about 0.002 to about 0.07, most preferably from about 0.005 to about 0.05. Such a suspension may be stirred under ambient conditions until adsorption of the co-ordination compound on the carbon surface has been accomplished. Under ambient conditions in acetone, for example, adsorption typically requires at least about 10 hours, more typically from about 24 to about 72 hours, most typically from about 36 to about 48 hours. After adsorption is accomplished the solids are filtered from the medium and dried, conveniently under vacuum. (5,10,15,20-tetraphenyl-21H,23H-porphine iron salts are sometimes referred to hereinafter as "FeTPP" which is intended to be generic to both ferric and ferrous salts and with counteranions other than halides. In the working examples, however, it is intended to refer specifically to the $FeCl_3$ salt).

The catalyst precursor obtained from the adsorption step is pyrolyzed to produce the Fe/N or Co/N on carbon redox catalyst. Pyrolysis is conducted under an inert or reducing atmosphere at a temperature of at least about 600° C., preferably from about 600° to about 1000° C., most preferably about 800° C. The particulate carbon bearing the Fe or Co complex and its pyrolysis products is preferably subjected to such pyrolysis conditions for a period of at least about 60 minutes, more preferably from about 80 to about 150 minutes, even more preferably from about 100 to about 140 minutes.

Upon pyrolysis, metal and nitrogen may be chemically bound to the support or trapped in pores, film or other surface microstructure which effectively fixes both metal and nitrogen to the surface. Where metal and nitrogen are chemically bound to the carbon surface, each may be directly bound to the carbon support, or nitrogen may be bound to Fe or Co that is bound to the support, or vice versa. Whatever the exact chemical structure, the composition of bound metal and nitrogen is believed to function as a transition metal active phase that promotes reduction of oxygen. Generally, it is understood that the metal and nitrogen are present in the form of a complex comprising metal nitrides, metal carbides, metal oxides, nitride-carbides, etc. Whether serving as an active phase and/or promoting activity at other sites, the transition metal/nitrogen composition obtained by pyrolysis may comprise one or more of such species. Regardless of the precise surface/activity relationships, the pyrolytic formation of this composition results in the creation of active sites which have been demonstrated to be more effective for oxygen reduction than the carbon support alone. Where a porous, particulate carbon support is used, it has been found that the bound transition metal/nitrogen composition is substantially evenly distributed throughout the carbon particle, not merely concentrated at the geometric surface. The surface of the carbon body is substantially devoid of any discrete transition metal particles having a principal dimension greater than about 5 µm.

The transition metal/nitrogen composition preferably comprises at least about 0.2%, preferably from about 0.4% to about 15%, and more preferably from about 0.4% to about 6% by weight of the catalyst. Iron, cobalt, or (Fe+Co) of the transition metal/nitrogen active phase is bound to the carbon support in a proportion of at least about 0.1% by weight, more preferably from about 0.1% to about 10% by weight, more preferably from about 0.25% to about 7% by weight, more preferably from about 0.5% to about 5% by weight and even more preferably from about 0.2% to about 3% by weight, basis the carbon support as so modified. On the same basis, nitrogen of the transition metal/nitrogen composition is bound to the carbon in a proportion of about 0.01% by weight, preferably from about 0.01% to about 10% by weight, more preferably from about 0.1% to about 7% by weight, more preferably from about 1% to about 5% by weight and even more preferably from about 0.2% to about 3% by weight. Generally, the ratio of Fe, Co or (Fe+Co) to N in the transition metal/nitrogen complex is from about 1:4 and about 3:1.

Analysis of the transition metal/nitrogen complex by Mössbauer spectroscopy indicates a complex structure of the transition metal/nitrogen composition formed on pyrolysis. In the case of the pyrolysis of a co-ordination compound comprising an iron salt with organic nitrogen containing ligands such as FeTPP on a particulate carbon support, a typical overall composition of the transition metal/nitrogen complex appears to be substantially the following:

| | |
|---|---|
| ξ-Fe$_3$N-like nitride | 30–70 wt. % |
| superparamagnetic iron | 5–20 wt. % |
| α-iron | 15–25 wt. % |
| isolated iron atoms | 10–20 wt. % |

However, other species including iron carbides and other iron nitrides may also be present. Similar compositions are believed to be formed upon pyrolysis of co-ordination compounds comprising cobalt and an organic nitrogen containing ligand. While sometimes referred to herein as an "active phase," the product of pyrolysis may actually comprise plural solid phases in a highly complex microstructure. Whatever its exact makeup, the product of the pyrolysis is referred to herein as the "transition metal/nitrogen composition," or specifically as the "Fe/N" or "Co/N" composition.

Optionally, the transition metal/nitrogen composition on carbon can be subjected to an acid wash before use as a catalyst for an oxidation reaction. Acid washing of the catalyst, e.g., with 0.2% by weight hydrochloric acid, has been found to remove a substantial fraction of iron from the catalyst surface, but does not have a proportionate effect on catalyst activity.

Other methods may be used in preparing the Fe/N or Co/N on carbon catalysts of the present invention. For example, a source of Fe or Co, such as a salt, oxide or hydroxide, can be pyrolyzed on a carbon support in the presence of a nitrogen source. Preferably, the Fe or Co salt, oxide or hydroxide is subjected to a reduction step prior to contact with the nitrogen source, or simultaneously therewith. Reduction is typically conducted at a temperature in the range of from about 400° to about 1000° C., preferably from about 500° to about 900° C., most preferably about 600° C., in the presence of reducing gas such as hydrogen. After reduction, the Fe/C precursor is pyrolyzed in the presence of a nitrogen source. The nitrogen source need not be initially coordinated to the Fe or Co, though co-ordination bonding may arise incident to contact of the Fe or Co salt with the nitrogen source under pyrolysis conditions. Advantageously, a vapor phase nitrogen source is maintained in contact with the Fe/C precursor during the pyrolysis. Suitable vapor phase nitrogen sources include compounds selected from the group consisting of ammonia, volatile amines, and volatile nitrites. Preferred vapor phase nitrogen sources include compounds selected from the group consisting of ammonia, ethylenediamine, isopropylamine, dimethylamine, acetonitrile and propionitrile.

Pyrolysis is conducted at a temperature of from about 400° to about 1200° C., preferably from about 600° to about 1100° C., most preferably about 1000° C. In this embodiment of the invention, it is important to maintain an adequate supply of the vapor phase nitrogen source in contact with the carbon support to replenish that which has reacted during pyrolysis. An adequate supply of the nitrogen source can be assured, and mass transfer of nitrogen to the carbon surface promoted, by passing a stream of the vapor phase nitrogen source through the pyrolysis zone while maintaining the zone under pyrolysis conditions and substantially free of oxidizing gases.

Still other methods can be used for producing the Fe/N or Co/N on carbon catalyst. For example, an iron or cobalt salt comprising a nitrogen containing anion may be deposited on a carbon support and thereafter pyrolyzed. Salts that can be used in such a process include cyanides and amino acid salts. However, to provide an adequate supply of nitrogen, pyrolysis should be conducted under an atmosphere in which a substantial partial pressure of the nitrogen source is maintained. Otherwise, the volatilization of nitrogen compounds from the carbon surface under pyrolysis conditions will not leave a sufficient source of nitrogen on the surface to create the concentration of active sites that are desired for the catalytic reduction of oxygen. In yet another method, the metal and nitrogen can be sputtered onto a carbon surface, or metal, nitrogen and carbon can be sputtered onto an inert support.

Catalysts comprising a transition metal/nitrogen composition bound to a carbon support have been demonstrated to exhibit a substantially enhanced efficacy for the reduction of molecular oxygen as compared to the carbon support alone. This may be demonstrated by subjecting the catalyst to cyclic voltammetric reduction of oxygen. For example, when cyclic voltammetry in the reduction of molecular oxygen is conducted in an electrolytic medium consisting of 0.1M H$_3$PO$_4$, a catalyst prepared from Fe(III)/tetraphenylporphyrin on carbon typically exhibits an increased reduction current relative to the untreated carbon support under reference conditions wherein the catalyst serves as an electrode that is cycled in the range of +0.5 to +0.1 volts vs. an Ag/AgCl electrode.

For use in reactions such as the oxidation of N-(phosphonomethyl)iminodiacetic acid to N-(phosphonomethyl)glycine, the redox catalyst of this invention preferably further comprises a noble metal deposited over the Fe/N and/or Co/N modified carbon support. In this case, formation of the Fe/N and/or Co/N composition is not only believed to provide active sites for oxygen reduction, but further provides a modified carbon support for a further active phase comprising noble metal that catalyzes transfer of electrons from an organic substrate to be oxidized. It has been found that Fe/N and/or Co/N on carbon, or in fact a carbon catalyst alone, is effective for the selective oxidative cleavage of one of the two carboxymethyl substituents of the N-(phosphonomethyl)iminodiacetic acid substrate, wherein carbon sites are believed to catalyze electron transfer from the substrate molecule. However, neither the unmodified nor the modified carbon is an entirely satisfactory catalyst for the further oxidation of both the $C_1$ by-products of the oxidative cleavage, i.e., formaldehyde and formic acid. Carbon alone has very little activity in catalyzing oxidation of $C_1$ compounds. The Fe/N or Co/N modified carbon catalyst of the invention has demonstrated some improvement for this purpose over carbon alone, but may still not be as active as may be desired. Unless the formaldehyde is effectively removed from the reaction zone, it tends to react with N-(phosphonomethyl)glycine to produce an undesired by-product, N-methyl-N-(phosphonomethyl)glycine ("NMG"), thereby reducing yields, reducing productivity, and compromising product quality.

Where the catalyst comprises a noble metal over a modified support comprising Fe/N and/or Co/N on carbon, it has not only been proven effective for the oxidation of N-(phosphonomethyl)iminodiacetic acid to N-(phosphonomethyl)glycine, but has also been demonstrated to be highly effective in the oxidation of organic compounds that are not readily amenable to oxidation in the presence of the Fe/N or Co/N on carbon alone, notably the formaldehyde produced as a by-product of the oxidative cleavage of N-(phosphonomethyl)iminodiacetic acid. Novel catalysts comprising a noble metal over Fe/N/carbon or Co/N/carbon have further been demonstrated to promote the oxidation of N-(phosphonomethyl)iminodiacetic acid to N-(phosphonomethyl)glycine at rates and productivity much enhanced over the rates found attainable with the otherwise highly desirable catalysts described in U.S. Pat. No. 6,417,133. However, the relative rate of over-oxidation, i.e., oxidation of product N-(phosphonomethyl)glycine to aminomethylphosphonic acid, is low, so the oxidation reaction mixture has a low aminomethylphosphonic acid as well as a low N-methyl-N-(phosphonomethyl)glycine content. Thus high yields and a high quality N-(phosphonomethyl)glycine product may be obtained.

In preparation of the novel catalysts of the invention, it is important that the Fe/N and/or Co/N active phase be deposited before deposition of the noble metal, and before deposition of any promoter that is alloyed with or associated with the noble metal. If the noble metal is deposited first, the above described methods for depositing the Fe/N or Co/N active phase tend to poison or otherwise deactivate the noble metal phase.

The noble metal is preferably a platinum group metal such as platinum, palladium, rhodium, iridium, osmium, ruthenium or combinations thereof. Because platinum is for many purposes the most preferred noble metal, the following discussion is directed primarily to embodiments using platinum. It should be understood, however, that the same discussion is generally applicable to the other noble metals and combinations thereof. It also should be understood that the term "noble metal" as used herein means the noble metal in its elemental state as well as the noble metal in any of its various oxidation states.

As described in U.S. Pat. No. 6,417,133, oxygen-containing functional groups (e.g., carboxylic acids, ethers, alcohols, aldehydes, lactones, ketones, esters, amine oxides, and amides) at the surface of the support increase noble metal leaching and potentially increase noble metal sintering during liquid phase oxidation reactions, thus reducing the ability of the catalyst to oxidize oxidizable substrates, particularly formaldehyde during the N-(phosphonomethyl) iminodiacetic acid oxidation. As used herein, an oxygen-containing functional group is "at the surface of the carbon support" if it is bound to an atom of the carbon of the support and is able to chemically or physically interact with compositions within the reaction mixture or with metal atoms deposited on a modified support.

Many of the oxygen-containing functional groups that reduce noble metal resistance to leaching and sintering and reduce the activity of the catalyst desorb from the carbon support as carbon monoxide when the catalyst is heated at a high temperature (e.g., 900° C.) in an inert atmosphere (e.g., helium or argon). Thus, measuring the amount of CO desorption from a fresh catalyst (i.e., a catalyst that has not previously been used in a liquid phase oxidation reaction) under high temperatures is one method that may be used to analyze the surface of the catalyst to predict noble metal retention and maintenance of catalyst activity. One way to measure CO desorption is by using thermogravimetric analysis with in-line mass spectroscopy ("TGA-MS"). Preferably, no more than about 1.2 mmole of carbon monoxide per gram of catalyst desorb from the catalyst when a dry, fresh sample of the catalyst in a helium atmosphere is subjected to a temperature which is increased from about 20° to about 900° C. at about 10° C. per minute, and then held constant at about 900° C. for about 30 minutes. More preferably, no more than about 0.7 mmole of carbon monoxide per gram of fresh catalyst desorb under those conditions, even more preferably no more than about 0.5 mmole of carbon monoxide per gram of fresh catalyst desorb, and most preferably no more than about 0.3 mmole of carbon monoxide per gram of fresh catalyst desorb. A catalyst is considered "dry" when the catalyst has a moisture content of less than about 1% by weight. Typically, a catalyst may be dried by placing it into a $N_2$ purged vacuum of about 25 inches of Hg and a temperature of about 120° C. for about 16 hours.

Measuring the number of oxygen atoms at the surface of a fresh catalyst support is another method which may be used to analyze the catalyst to predict noble metal retention and maintenance of catalytic activity. Using, for example, x-ray photoelectron spectroscopy, a surface layer of the support which is about 50 Å in thickness is analyzed. Presently available equipment used for x-ray photoelectron spectroscopy typically is accurate to within ±20%. Typically, a ratio of carbon atoms to oxygen atoms at the surface (as measured by presently available equipment for x-ray photoelectron spectroscopy) of at least about 20:1 (carbon atoms:oxygen atoms) is suitable. Preferably, however, the ratio is at least about 30:1, more preferably at least about 40:1, even more preferably at least about 50:1, and most preferably at least about 60:1. In addition, the ratio of oxygen atoms to metal atoms at the surface (again, as measured by presently available equipment for x-ray photoelectron spectroscopy) preferably is less than about 8:1 (oxygen atoms:metal atoms). More preferably, the ratio is less than about 7:1, even more preferably less than about 6:1, and most preferably less than about 5:1.

The concentration of the noble metal deposited at the surface of the modified carbon support may vary within wide limits. Preferably, it is in the range of from about 0.5% to about 20% by weight ([mass of noble metal÷total mass of catalyst]×100%), more preferably from about 2.5% to about 10% by weight, and most preferably from about 3% to about 7.5% by weight. If concentrations less than 0.5% by weight are used, the catalyst may be ineffective for the oxidation of certain substrates, e.g., by-product formaldehyde from the oxidation of N-(phosphonomethyl)iminodiacetic acid. On the other hand, at concentrations greater than about 20% by weight, layers and clumps of noble metal tend to form. Thus, there are fewer surface noble metal atoms per total amount of noble metal used. This tends to reduce the activity of the catalyst and is an uneconomical use of the costly noble metal.

The dispersion of the noble metal at the surface of the modified carbon support preferably is such that the concentration of surface noble metal atoms is from about 10 to about 400 μmole/g (μmole of surface noble metal atoms per gram of catalyst), more preferably, from about 10 to about 150 μmole/g, and most preferably from about 15 to about 100 μmole/g. This may be determined, for example, by measuring chemisorption of $H_2$ or CO using a Micromeritics ASAP 2010C (Micromeritics, Norcross, Ga.) or an Altamira AMI100 (Zeton Altamira, Pittsburgh, Pa.).

Preferably, the noble metal is at the surface of the modified carbon support in the form of metal particles. At least about 90% (number density) of the noble metal particles at the surface of the modified support are preferably from about 0.5 to about 35 nm in their largest dimension, more preferably from about 1 to about 20 nm in their largest dimension, and most preferably from about 1.5 to about 10 nm in their largest dimension. In a particularly preferred embodiment, at least about 80% of the noble metal particles at the surface of the modified support are from about 1 to about 15 nm in their largest dimension, more preferably from about 1.5 to about 10 nm in their largest dimension, and most preferably from about 1.5 to about 7 nm in their largest dimension. If the noble metal particles are too small, there tends to be an increased amount of leaching when the catalyst is used in an environment that tends to solubilize noble metals, as is the case when oxidizing N-(phosphonomethyl)iminodiacetic acid to form N-(phosphonomethyl) glycine. On the other hand, as the particle size increases, there tends to be fewer noble metal surface atoms per total amount of noble metal used. As discussed above, this tends to reduce the activity of the catalyst and is an uneconomical use of the noble metal.

In addition to the noble metal, at least one promoter may be at the surface of the modified carbon support. Although the promoter typically is deposited onto the surface of the modified carbon support, other sources of promoter may be used (e.g., the carbon support itself may naturally contain a promoter). A promoter tends to increase catalyst selectivity, activity, and/or stability. A promoter additionally may reduce noble metal leaching.

The promoter may, for example, be an additional noble metal(s) at the surface of the support. For example, ruthenium and palladium have been found to act as promoters on a catalyst comprising platinum deposited at a carbon support surface. The promoter(s) alternatively may be, for example, a metal selected from the group consisting of tin (Sn), cadmium (Cd), magnesium (Mg), manganese (Mn), nickel (Ni), aluminum (Al), cobalt (Co), bismuth (Bi), lead (Pb), titanium (Ti), antimony (Sb), selenium (Se), iron (Fe), rhenium (Re), zinc (Zn), cerium (Ce), zirconium (Zr), tellurium (Te), and germanium (Ge). Preferably, the promoter is selected from the group consisting of bismuth, iron, tin, tellurium and titanium. In a particularly preferred embodiment, the promoter is tin. In another particularly preferred embodiment, the promoter is iron. In an additional preferred embodiment, the promoter is titanium. In a further particularly preferred embodiment, the catalyst comprises both iron and tin. Use of iron, tin, or both generally (1) reduces noble metal leaching for a catalyst used over several cycles, and (2) tends to increase and/or maintain the activity of the catalyst when the catalyst is used to effect the oxidation of N-(phosphonomethyl)iminodiacetic acid. Catalysts comprising iron generally are most preferred because they tend to have the greatest activity and stability with respect to formaldehyde and formic acid oxidation.

It will be understood that the promoter is metal that is alloyed or associated with the noble metal active phase. Iron or cobalt present in or on the carbon support as part of the pyrolytic Fe/N or Co/N composition is not understood to function as a promoter of the noble metal for transfer of electrons from the substrate to be oxidized, but primarily to constitute or provide sites for transfer of electrons to an $O_2$ molecule to be reduced. As described in detail below, the noble metal with which the promoter is alloyed or associated is typically present in the form of crystallites on the carbon surface, whereas the Fe or Co of the transition metal/ nitrogen composition is more intimately associated with or bound to the carbon atoms of the support, and more uniformly distributed throughout the catalyst particle.

In one preferred embodiment, the promoter is more easily oxidized than the noble metal. A promoter is "more easily oxidized" if it has a lower first ionization potential than the noble metal. First ionization potentials for the elements are widely known in the art and may be found, for example, in the *CRC Handbook of Chemistry and Physics* (CRC Press, Inc., Boca Raton, Fla.).

The amount of promoter at the surface of the modified carbon support (whether associated with the carbon surface itself, metal, or a combination thereof) may vary within wide limits depending on, for example, the noble metal and promoter used. Typically, the weight percentage of the promoter is at least about 0.05% ([mass of promoter÷total mass of the catalyst]×100%). The weight percent of the promoter preferably is from about 0.05 to about 10%, more preferably from about 0.1 to about 10%, still more preferably from about 0.1 to about 2%, and most preferably from about 0.2 to about 1.5%. When the promoter is tin, the weight percent most preferably is from about 0.5 to about 1.5%. Promoter weight percentages less than 0.05% generally do not promote the activity of the catalyst over an extended period of time. On the other hand, concentrations of promoter greater than about 10% by weight tend to decrease the activity of the catalyst.

The molar ratio of noble metal to promoter may also vary widely, depending on, for example, the noble metal and promoter used. Preferably, the ratio is from about 1000:1 to about 0.01:1; more preferably from about 150:1 to about 0.05:1; still more preferably from about 50:1 to about 0.05:1; and most preferably from about 10:1 to about 0.05:1. For example, a preferred catalyst comprising platinum and iron has a molar ratio of platinum to iron of about 3:1.

In a particularly preferred embodiment of this invention, the noble metal (e.g., Pt) is alloyed with at least one promoter (e.g., Sn, Fe, or both) to form alloyed metal particles. A catalyst comprising a noble metal alloyed with at least one promoter tends to have all the advantages discussed above with respect to catalysts comprising a promoter. It has been found in accordance with this invention, however, that catalysts comprising a noble metal alloyed with at least one promoter tend to exhibit greater resistance to promoter leaching and further stability from cycle to cycle with respect to formaldehyde and formic acid oxidation.

The term "alloy" encompasses any metal particle comprising a noble metal and at least one promoter, irrespective of the precise manner in which the noble metal and promoter atoms are disposed within the particle (although it is generally preferable to have a portion of the noble metal atoms at the surface of the alloyed metal particle). The alloy may be, for example, any of the following:

1. An intermetallic compound. An intermetallic compound is a compound comprising a noble metal and a promoter (e.g., $Pt_3Sn$).

2. A substitutional alloy. A substitutional alloy has a single, continuous phase, irrespective of the concentrations of the noble metal and promoter atoms. Typically, a substitutional alloy contains noble metal and promoter atoms which are similar in size (e.g., platinum or platinum and palladium). Substitutional alloys are also referred to as "monophasic alloys."

3. A multiphasic alloy. A multiphasic alloy is an alloy that contains at least two discrete phases. Such an alloy may contain, for example $Pt_3Sn$ in one phase, and tin dissolved in platinum in a separate phase.

4. A segregated alloy. A segregated alloy is a metal particle wherein the particle stoichiometry varies with distance from the surface of the metal particle.

5. An interstitial alloy. An interstitial alloy is a metal particle wherein the noble metal and promoter atoms are combined with non-metal atoms, such as boron, carbon, silicon, nitrogen, phosphorus, etc.

Preferably, at least about 80% (number density) of the alloyed metal particles are from about 0.5 to about 35 nm in their largest dimension, more preferably from about 1 to about 20 nm in their largest dimension, still more preferably from about 1 to about 15 nm in their largest dimension, and most preferably from about 1.5 to about 7 nm in their largest dimension.

The alloyed metal particles need not have a uniform composition; the compositions may vary from particle to particle, or even within the particles themselves. In addition, the catalyst may further comprise particles consisting of the noble metal alone or the promoter alone. Nevertheless, it is preferred that the composition of metal particles be substantially uniform from particle to particle and within each particle, and that the number of noble metal atoms in intimate contact with promoter atoms be maximized. It is also preferred, although not essential, that the majority of noble metal atoms be alloyed with a promoter, and more preferred that substantially all of the noble metal atoms be alloyed with a promoter. It is further preferred, although not essential, that the alloyed metal particles be uniformly distributed at the surface of the carbon support.

Regardless of whether the promoter is alloyed to the noble metal, it is presently believed that the promoter tends to become oxidized if the catalyst is exposed to an oxidant over a period of time. For example, an elemental tin promoter tends to oxidize to form $Sn(II)O$, and $Sn(II)O$ tends to oxidize to form $Sn(IV)O_2$. This oxidation may occur, for example, if the catalyst is exposed to air for more than about 1 hour. Although such promoter oxidation has not been observed to have a significant detrimental effect on noble metal leaching, noble metal sintering, catalyst activity, or catalyst stability, it does make analyzing the concentration of detrimental oxygen-containing functional groups at the surface of the carbon support more difficult. For example, as discussed above, the concentration of detrimental oxygen-containing functional groups (i.e., oxygen-containing functional groups that reduce noble metal resistance to leaching and sintering, and reduce the activity of the catalyst) may be determined by measuring (using, for example, TGA-MS) the amount of CO that desorbs from the catalyst under high temperatures in an inert atmosphere. However, it is presently believed that when an oxidized promoter is present at the surface, the oxygen atoms from the oxidized promoter tend to react with carbon atoms of the support at high temperatures in an inert atmosphere to produce CO, thereby creating the illusion of more detrimental oxygen-containing functional groups at the surface of the support than actually exist. Such oxygen atoms of an oxidized promoter also can interfere with obtaining a reliable prediction of noble metal leaching, noble metal sintering, and catalyst activity from the simple measurement (via, for example, x-ray photoelectron spectroscopy) of oxygen atoms at the catalyst surface.

Thus, when the catalyst comprises at least one promoter which has been exposed to an oxidant and thereby has been oxidized (e.g., when the catalyst has been exposed to air for more than about 1 hour), it is preferred that the promoter first be substantially reduced (thereby removing the oxygen atoms of the oxidized promoter from the surface of the catalyst) before attempting to measure the amount of detrimental oxygen-containing functional groups at the surface of the carbon support. This reduction preferably is achieved by heating the catalyst to a temperature of about 500° C. for about 1 hour in an atmosphere consisting essentially of $H_2$. The measurement of detrimental oxygen-containing functional groups at the surface preferably is performed (a) after this reduction, and (b) before the surface is exposed to an oxidant following the reduction. Most preferably, the measurement is taken immediately after the reduction.

The preferred concentration of metal particles at the surface of the modified support depends, for example, on the size of the metal particles, the specific surface area of the carbon support, and the concentration of noble metal on the catalyst. It is presently believed that, in general, the preferred concentration of metal particles is roughly from about 3 to about 1,500 particles/$\mu m^2$ (i.e., number of metal particles per $\mu m^2$ of surface of carbon support), particularly where: (a) at least about 80% (number density) of the metal particles are from about 1.5 to about 7 nm in their largest dimension, (b) the carbon support has a specific surface area of from about 750 to about 2100 $m^2/g$ (i.e., $m^2$ of surface of support per gram of modified carbon support), and (c) the concentration of noble metal at the carbon support surface is from about 1% to about 10% by weight ([mass of noble metal÷total mass of catalyst]×100%). In more preferred embodiments, narrower ranges of metal particle concentrations and noble metal concentrations are desired. In one such embodiment, the concentration of metal particles is from about 15 to about 800 particles/$\mu m^2$, and the concentration of noble metal at the carbon support surface is from about 2% to about 10% by weight. In an even more preferred embodiment, the concentration of metal particles is from about 15 to about 600 particles/$\mu m^2$, and the concentration of noble metal at the support surface is from about 2% to about 7.5% by weight. In the most preferred embodiment, the concentration of the metal particles is from about 15 to about 400 particles/$\mu M^2$, and the concentration of noble metal at the support surface is about 5% by weight. The concentration of metal particles at the surface of the modified carbon support may be measured using methods known in the art.

Methods used to deposit the noble metal and/or promoter over the modified carbon support are generally known in the art and further described in U.S. Pat. No. 6,417,133, the text of which is expressly incorporated herein by reference. For example, suitable methods for deposition of the noble metal and/or promoter include liquid phase methods such as reaction deposition techniques (e.g., deposition via reduction of the metal compounds, and deposition via hydrolysis of the metal compounds), ion exchange techniques, excess solution impregnation, and incipient wetness impregnation; vapor phase methods such as physical deposition and chemical deposition; precipitation; electrochemical deposition; and electroless deposition. See generally, Cameron et al., "Carbons as Supports for Precious Metal Catalysts," *Catalysis Today*, 7, 113–137 (1990).

In a preferred embodiment, the modified carbon support surface is reduced after deposition of the noble metal as described in U.S. Pat. No. 6,417,133 (incorporated herein by reference) to produce a deeply reduced catalyst characterized by the above-described CO desorption and C/O surface ratio parameters. In particular, the surface of the catalyst is reduced, for example, by heating the surface at a temperature of at least about 400° C. It is especially preferred to conduct this heating in a non-oxidizing environment (e.g., nitrogen, argon, or helium), even more preferably while exposing the catalyst to a reducing environment (e.g., a gas phase reducing agent such as $H_2$, ammonia or carbon monoxide). Preferably, the surface is heated at a temperature of at least about 500° C., more preferably from about 550° to about 1200° C., and even more preferably from about 550° to about 900° C.

It is important to note that, in embodiments of the invention wherein the surface of the modified carbon support is reduced after noble metal deposition, it may be possible to prepare the modified carbon support at a lower temperature than as described above. For example, when the modified carbon support is prepared by first depositing a co-ordination compound comprising an Fe or Co salt and ligands containing nitrogen as described above, it may be possible to fix the Fe/N or Co/N active phase on the carbon support by pyrolysis at lower temperatures and/or for shorter durations than as described above. Thus, high temperature treatment in reducing the catalyst surface after deposition of the noble metal and/or promoter, as described in U.S. Pat. No. 6,417,133, serves as a further pyrolysis to provide the Fe/N or Co/N active phase and the noble metal active phase of the catalyst.

The catalysts of the invention can be used in a wide variety of redox reactions. In certain applications as referred to above, it is highly preferred that the catalyst include a noble metal phase. However, the modified carbon bodies comprising a transition metal and nitrogen are also effective for the oxidation of a wide variety of organic substrates even in the absence of a noble metal. For example, the modified carbon bodies may serve for example as oxidation catalysts in various commercial oxidation processes such as the partial oxidation of hydrocarbons to produce aldehydes, ketones and carboxylic acids. In particulate or agglomerated form, the modified carbon can constitute a fixed or fluid bed for gas phase oxidations; in slurry form, the modified carbon can serve to catalyze liquid phase oxidations. The novel catalysts of the invention, preferably comprising a noble metal active phase over a support comprising carbon and a transition metal/nitrogen composition, are advantageously used in gas phase reactions such as benzyl alcohol to benzaldehyde, glucose to gluconic acid, and various carbohydrate oxidations. Examples of liquid phase reactions in which the noble metal-bearing catalysts can be used include the oxidation of alcohols and polyols to form aldehydes, ketones, and acids (e.g., the oxidation of 2-propanol to form acetone, and the oxidation of glycerol to form glyceraldehyde, dihydroxyacetone, or glyceric acid); the oxidation of aldehydes to form acids (e.g., the oxidation of formaldehyde to form formic acid, and the oxidation of furfural to form 2-furan carboxylic acid); the oxidation of tertiary amines to form secondary amines (e.g., the oxidation of nitrilotriacetic acid ("NTA") to form iminodiacetic acid ("IDA")); the oxidation of secondary amines to form primary amines (e.g., the oxidation of IDA to form glycine); and the oxidation of various acids (e.g., formic acid or acetic acid) to form carbon dioxide and water.

The catalysts of the invention, preferably comprising a noble metal over a modified carbon support comprising carbon having the transition metal/nitrogen composition thereon, is also advantageously used in the oxidation of a tertiary amine substrate corresponding to a compound of Formula I having the structure:

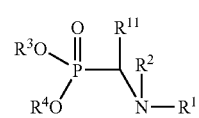

[Formula I]

wherein $R^1$ is selected from the group consisting of $R^5OC(O)CH_2$— and $R^5OCH_2CH_2$—, $R^2$ is selected from the group consisting of $R^5OC(O)CH_2$—, hydrocarbyl, substituted hydrocarbyl, acyl, —$CHR^6PO_3R^7R^8$, and —$CHR^9SO_3R^{10}$, $R^6$, $R^9$ and $R^{11}$ are selected from the group consisting of hydrogen, alkyl, halogen and —$NO_2$, and $R^3$, $R^4$, $R^5$, $R^7$, $R^8$ and $R^{10}$ are independently selected from the group consisting of hydrogen, hydrocarbyl, substituted hydrocarbyl and a metal ion. In certain embodiments, preferably $R^1$ comprises $R^5OC(O)CH_2$—, $R^{11}$ is hydrogen, and $R^5$ is selected from hydrogen and an agronomically acceptable cation. More preferably in such embodiments, $R^2$ is selected from the group consisting of $R^5OC(O)CH_2$—, acyl, hydrocarbyl and substituted hydrocarbyl.

In a particularly preferred application, the novel noble metal over Fe/N/carbon or Co/N/carbon catalysts of the invention are used in the catalytic oxidation of N-(phosphonomethyl)iminodiacetic acid to N-(phosphonomethyl)glycine. In this reaction, the noble-metal bearing catalysts of the present invention have been demonstrated to substantially enhance the rate of conversion as compared to the otherwise highly preferred catalysts described in U.S. Pat. No. 6,417,133.

As noted above, the oxidation of N-(phosphonomethyl) iminodiacetic acid results not only in the formation of N-(phosphonomethyl)glycine but also the $C_1$ by-products formaldehyde and formic acid. As the $C_1$ by-products are formed, formaldehyde and formic acid are preferably further oxidized to carbon monoxide, thereby to avoid excessive formation of by-product N-methyl-N-(phosphonomethyl) glycine. The overall reactions involved in the process are accomplished via complementary oxidation and reduction steps which may be summarized as follows:

Oxidation Reactions

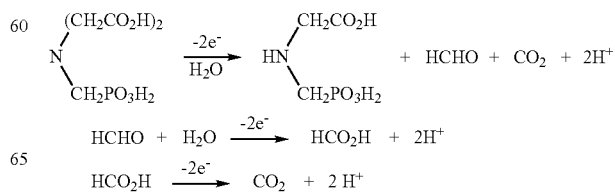

-continued

Reduction Reaction

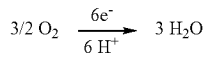

Figure 13:
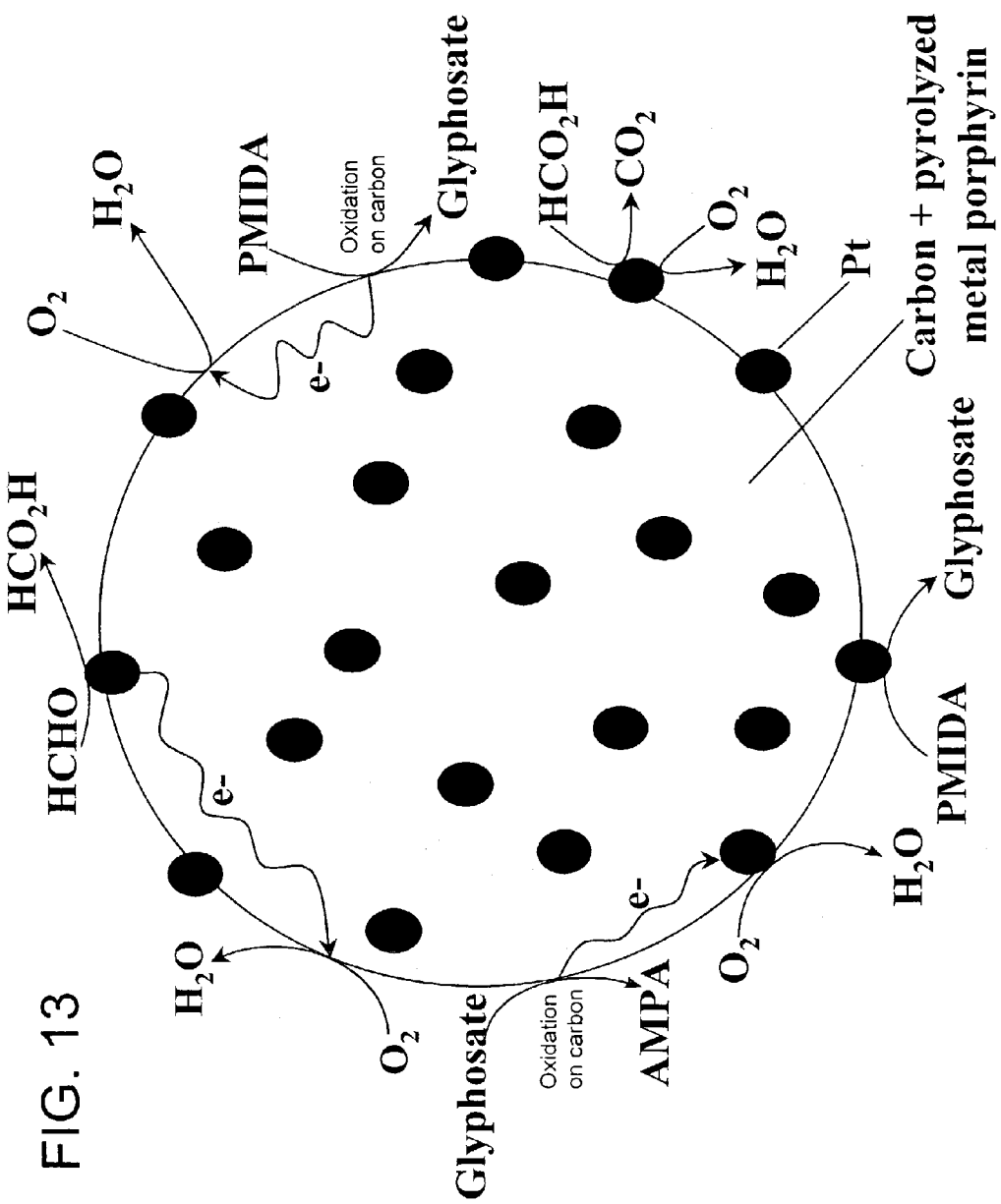
FIG. 13 is a schematic illustration of the equivalent anodic and cathodic half cell reactions believed to occur at the surface of the catalyst in the non-electrolytic oxidation of N-(phosphonomethyl)iminodiacetic acid to N-(phosphonomethyl)glycine by catalytic reaction with molecular oxygen in accordance with a preferred process of the invention.

The oxidation of N-(phosphonomethyl)iminodiacetic acid to N-(phosphonomethyl)glycine is believed to occur at both carbon sites and noble metal sites of the catalyst, while the oxidation of formaldehyde to formic acid takes place primarily on the noble metal. The complementary reduction of oxygen, which drives the oxidation reactions, is believed to take place not only at the noble metal sites of the catalyst but also on the carbon surface carrying finely dispersed pyrolyzed Fe/N compounds that may also include bound carbon. This is illustrated schematically in FIG. 13 which shows the oxidation of N-(phosphonomethyl)iminodiacetic acid to N-(phosphonomethyl)glycine at both Pt and other sites, the oxidation of formaldehyde to formic acid and the further oxidation of formic acid to $Co_2$ and water which takes place primarily at the Pt sites, and the reduction of oxygen which is understood to take place predominantly at Pt sites or sites of an active Fe/N phase that had been produced by pyrolysis of an FeTPP complex on the carbon support during the preparation of the catalyst. The reactions are balanced by transfer of electrons from oxidation to reduction sites through the bulk of the catalyst body. The presence of the pyrolyzed Fe/N compounds is believed to enhance the reaction by supplementing the oxygen reduction capability of the catalyst.

To begin the N-(phosphonomethyl)iminodiacetic acid oxidation reaction, it is preferable to charge the reactor with the N-(phosphonomethyl)iminodiacetic acid reagent (i.e., N-(phosphonomethyl)iminodiacetic acid or a salt thereof), catalyst, and a solvent in the presence of oxygen. The solvent is most preferably water, although other solvents (e.g., glacial acetic acid) are suitable as well.

The reaction may be carried out in a wide variety of batch, semi-batch, and continuous reactor systems. The configuration of the reactor is not critical. Suitable conventional reactor configurations include, for example, stirred tank reactors, fixed bed reactors, trickle bed reactors, fluidized bed reactors, bubble flow reactors, plug flow reactors, and parallel flow reactors. A further discussion of suitable reactor systems, particularly continuous reactor systems, may be found in U.S. Publication No. US-2002-0068836-A1, which is hereby incorporated by reference in its entirety.

When conducted in a continuous reactor system, the residence time in the reaction zone can vary widely depending on the specific catalyst and conditions employed. Typically, the residence time can vary over the range of from about 3 to about 120 minutes. Preferably, the residence time is from about 5 to about 90 minutes, and more preferably from about 5 to about 60 minutes. When conducted in a batch reactor, the reaction time typically varies over the range of from about 15 to about 120 minutes. Preferably, the reaction time is from about 20 to about 90 minutes, and more preferably from about 30 to about 60 minutes.

In a broad sense, the oxidation reaction may be practiced in accordance with the present invention at a wide range of temperatures, and at pressures ranging from sub-atmospheric to super-atmospheric. Use of mild conditions (e.g., room temperature and atmospheric pressure) have obvious commercial advantages in that less expensive equipment may be used. However, operating at higher temperatures and super-atmospheric pressures, while increasing plant costs, tends to improve phase transfer between the liquid and gas phase and increase the N-(phosphonomethyl)iminodiacetic acid oxidation reaction rate.

Preferably, the N-(phosphonomethyl)iminodiacetic acid reaction is conducted at a temperature of from about 20° to about 180° C., more preferably from about 50° to about 140° C., and most preferably from about 80° to about 110° C. At temperatures greater than about 180° C., the raw materials tend to begin to slowly decompose.

The pressure used during the N-(phosphonomethyl)iminodiacetic acid oxidation generally depends on the temperature used. Preferably, the pressure is sufficient to prevent the reaction mixture from boiling. If an oxygen-containing gas is used as the oxygen source, the pressure also preferably is adequate to cause the oxygen to dissolve into the reaction mixture at a rate sufficient such that the N-(phosphonomethyl)iminodiacetic acid oxidation is not limited due to an inadequate oxygen supply. The pressure preferably is at least equal to atmospheric pressure. More preferably, the oxygen partial pressure is from about 30 to about 500 psig, and most preferably from about 30 to about 130 psig.

The catalyst concentration preferably is from about 0.1% to about 10% by weight ([mass of catalyst÷total reaction mass]×100%). More preferably, the catalyst concentration preferably is from about 0.2% to about 5% by weight, and most preferably from about 0.3% to about 1.5% by weight. Concentrations greater than about 10% by weight are difficult to filter. On the other hand, concentrations less than about 0.1% by weight tend to produce unacceptably low reaction rates.

The concentration of N-(phosphonomethyl)iminodiacetic acid reagent in the feed stream is not critical. Use of a saturated solution of N-(phosphonomethyl)iminodiacetic acid reagent in water is preferred, although for ease of operation, the process is also operable at lesser or greater N-(phosphonomethyl)iminodiacetic acid reagent concentrations in the feed stream. If the catalyst is present in the reaction mixture in a finely divided form, it is preferred to use a concentration of reactants such that the N-(phosphonomethyl)glycine product remains in solution so that the catalyst can be recovered for re-use, for example, by filtration. On the other hand, greater concentrations tend to increase reactor through-put.

It should be recognized that, relative to many commonly-practiced commercial processes, this invention allows for greater temperatures and N-(phosphonomethyl)iminodiacetic acid reagent concentrations to be used to prepare N-(phosphonomethyl)glycine while minimizing by-product formation. In the commonly practiced commercial processes using a carbon-only catalyst, it is economically beneficial to minimize the formation of the NMG by-product formed by the reaction of N-(phosphonomethyl)glycine with the formaldehyde by-product. With these processes and catalysts, temperatures of from about 60° to about 90° C. and N-(phosphonomethyl)iminodiacetic acid reagent concentrations below about 9.0% by weight ([mass of N-(phosphonomethyl)iminodiacetic acid reagent÷total reaction mass]× 100%) typically are used to achieve cost effective yields and to minimize the generation of waste. At these temperatures, the maximum N-(phosphonomethyl)glycine solubility typically is less than 6.5%. However, with the oxidation catalyst and reaction process of this invention, the loss of noble metal from the catalyst and catalyst deactivation have been minimized and the formaldehyde is more effectively oxidized, thereby allowing for reaction temperatures as high as 180° C. or greater with N-(phosphonomethyl)iminodiacetic acid reagent solutions and slurries of the N-(phosphonomethyl)iminodiacetic acid reagent. The use of higher temperatures and reactor concentrations permits reactor throughput to be increased, reduces the amount of water that must be removed before isolation of the solid N-(phosphonomethyl) glycine, and reduces the cost of manufacturing N-(phosphonomethyl)glycine. This invention thus provides economic benefits over many commonly-practiced commercial processes.

Normally, a N-(phosphonomethyl)iminodiacetic acid reagent concentration of up to about 50% by weight ([mass of N-(phosphonomethyl)iminodiacetic acid reagent÷total reaction mass]×100%) may be used (especially at a reaction temperature of from about 200 to about 180° C.). Preferably, a N-(phosphonomethyl)iminodiacetic acid reagent concentration of up to about 25% by weight is used (particularly at a reaction temperature of from about 600 to about 150° C.). More preferably, a N-(phosphonomethyl)iminodiacetic acid reagent concentration of from about 12% to about 18% by weight is used (particularly at a reaction temperature of from about 100° to about 130° C.). N-(phosphonomethyl)iminodiacetic acid reagent concentrations below 12% by weight may be used, but their use is less economical because less N-(phosphonomethyl)glycine product is produced in each reactor cycle and more water must be removed and energy used per unit of N-(phosphonomethyl)glycine product produced. Lower temperatures (i.e., temperatures less than 100° C.) often tend to be less advantageous because the solubility of the N-(phosphonomethyl)iminodiacetic acid reagent and N-(phosphonomethyl)glycine product are both reduced at such temperatures.

The oxygen source for the N-(phosphonomethyl)iminodiacetic acid oxidation reaction may be any oxygen-containing gas or a liquid comprising dissolved oxygen. Preferably, the oxygen source is an oxygen-containing gas. As used herein, an "oxygen-containing gas" is any gaseous mixture comprising molecular oxygen which optionally may comprise one or more diluents which are non-reactive with the oxygen or with the reactant or product under the reaction conditions. Examples of such gases are air, pure molecular oxygen, or molecular oxygen diluted with helium, argon, nitrogen, or other non-oxidizing gases. For economic reasons, the oxygen source most preferably is air or pure molecular oxygen.

The oxygen may be introduced by any conventional means into the reaction medium in a manner which maintains the dissolved oxygen concentration in the reaction mixture at the desired level. If an oxygen-containing gas is used, it preferably is introduced into the reaction medium in a manner which maximizes the contact of the gas with the reaction solution. Such contact may be obtained, for example, by dispersing the gas through a diffuser such as a porous frit or by stirring, shaking, or other methods known to those skilled in the art.

The oxygen feed rate preferably is such that the N-(phosphonomethyl)iminodiacetic acid oxidation reaction rate is not limited by oxygen supply. If the dissolved oxygen concentration is too high, however, the catalyst surface tends to become detrimentally oxidized, which, in turn, tends to lead to more leaching and decreased formaldehyde activity (which, in turn, leads to more NMG being produced).

Generally, it is preferred to use an oxygen feed rate such that at least about 40% of the oxygen is utilized. More preferably, the oxygen feed rate is such that at least about 60% of the oxygen is utilized. Even more preferably, the oxygen feed rate is such that at least about 80% of the oxygen is utilized. Most preferably, the rate is such that at least about 90% of the oxygen is utilized. As used herein, the percentage of oxygen utilized equals: (the total oxygen consumption rate÷oxygen feed rate)×100%. The term "total oxygen consumption rate" means the sum of: (i) the oxygen consumption rate ("$R_i$") of the oxidation reaction of the N-(phosphonomethyl)iminodiacetic acid reagent to form the N-(phosphonomethyl)glycine product and formaldehyde, (ii) the oxygen consumption rate ("$R_{ii}$") of the oxidation reaction of formaldehyde to form formic acid, and (iii) the oxygen consumption rate ("$R_{iii}$") of the oxidation reaction of formic acid to form carbon dioxide and water.

In one embodiment of this invention, oxygen is fed into the reactor as described above until the bulk of N-(phosphonomethyl)iminodiacetic acid reagent has been oxidized, and then a reduced oxygen feed rate is used. This reduced feed rate preferably is used after about 75% of the N-(phosphonomethyl)iminodiacetic acid reagent has been consumed. More preferably, the reduced feed rate is used after about 80% of the N-(phosphonomethyl)iminodiacetic acid reagent has been consumed. The reduced feed rate may be achieved by purging the reactor with air, preferably at a volumetric feed rate which is no greater than the volumetric rate at which the pure molecular oxygen was fed before the air purge. The reduced oxygen feed rate preferably is maintained for a period of from about 2 to about 40 minutes, more preferably from about 5 to about 20 minutes, and most preferably from about 5 to about 15 minutes. While the oxygen is being fed at the reduced rate, the temperature preferably is maintained at the same temperature or at a temperature less than the temperature at which the reaction was conducted before the air purge. Likewise, the pressure is maintained at the same or at a pressure less than the pressure at which the reaction was conducted before the air purge. Use of a reduced oxygen feed rate near the end of the N-(phosphonomethyl)iminodiacetic acid reaction tends to reduce the amount of residual formaldehyde present in the reaction solution without producing detrimental amounts of aminomethylphosphonic acid by oxidizing the N-(phosphonomethyl)glycine product.

Reduced losses of noble metal may be observed with this invention if a sacrificial reducing agent is maintained or introduced into the reaction solution. Suitable reducing agents include formaldehyde, formic acid, and acetaldehyde. Most preferably, formic acid, formaldehyde, or mixtures thereof are used. Experiments conducted in accordance with this invention indicate that if small amounts of formic acid, formaldehyde, or a combination thereof are added to the reaction solution, the catalyst will preferentially effect the oxidation of the formic acid or formaldehyde before it effects the oxidation of the N-(phosphonomethyl)iminodiacetic acid reagent, and subsequently will be more active in effecting the oxidation of formic acid and formaldehyde during the N-(phosphonomethyl)iminodiacetic acid oxidation. Preferably from about 0.01% to about 5.0% by weight ([mass of formic acid, formaldehyde, or a combination thereof÷total reaction mass]×100%) of sacrificial reducing agent is added, more preferably from about 0.01% to about 3.0% by weight of sacrificial reducing agent is added, and most preferably from about 0.01% to about 1.0% by weight of sacrificial reducing agent is added.

In one preferred embodiment, unreacted formaldehyde and formic acid are recycled back into the reaction mixture for use in subsequent cycles. In this instance, the recycle stream also may be used to solubilize the N-(phosphonomethyl)iminodiacetic acid reagent in the subsequent cycles.

Typically, the concentration of N-(phosphonomethyl)glycine in the product mixture may be as high as 40% by weight or more. Preferably, the N-(phosphonomethyl)glycine concentration is from about 5% to about 40% by weight, more preferably from about 8% to about 30% by weight, and still more preferably from about 9% to about 15% by weight. Concentrations of formaldehyde in the product mixture are typically less than about 0.5% by weight, more preferably less than about 0.3% by weight, and still more preferably less than about 0.15% by weight.

Following the oxidation, the catalyst preferably is subsequently separated from the product mixture by filtration. The N-(phosphonomethyl)glycine product may then be isolated by precipitation, for example, by evaporation of a portion of the water and cooling.

It should be recognized that the catalyst of this invention has the ability to be reused over several cycles, depending on how oxidized its surface becomes with use. Even after the catalyst becomes heavily oxidized, it may be reused by being reactivated. To reactivate a catalyst having a heavily oxidized surface, the surface preferably is first washed to remove the organics from the surface. It then preferably is reduced in the same manner that a catalyst is reduced after the noble metal is deposited onto the surface of the support, as described above.

In addition to their function as catalysts for the oxidation of N-(phosphonomethyl)iminodiacetic acid and other substrates with molecular oxygen, the catalysts of the invention may be used as electrode materials in electrocatalytic reactions, that can occur on carbon at less than or equal to about 0.6V vs. an Ag/AgCl electrode, including the electrocatalytic oxidation of N-(phosphonomethyl)iminodiacetic acid to N-(phosphonomethyl)glycine, and other liquid phase oxidation substrates as described hereinabove. In the oxidation of N-(phosphonomethyl)iminodiacetic acid, it is highly desirable if not essential that the catalyst include a noble metal deposited over a support modified by the presence of a transition metal/nitrogen composition of the type herein described. For certain other substrates the modified carbon may in itself function as an effective catalyst for the electrolytic reaction. The high dispersion of the active sites on the carbon surface provides very high reactivity and promotes rapid catalytic reactions.

The modified carbon supports and catalysts of the present invention having a transition metal/nitrogen composition thereon can also be used as cathode materials in a fuel cell. In operation, electrical energy is generated by supplying fuel in contact with an anode of the fuel cell and molecular oxygen in contact with a cathode thereof. The cathode comprises carbon bodies, a carbon monolith, or other carbon support modified to provide the aforesaid transition metal/nitrogen composition thereon. The fuel gives up electrons at the anode while oxygen is reduced at the cathode by electrons flowing through the circuit to the anode. A potential is generated between the electrodes effective for providing electrical energy to a load in the circuit such as a lamp, a motor, etc., between the anode and the cathode.

A carbon support modified by the presence of the transition metal/nitrogen composition may serve other functions as well, e.g., as an adsorbent for the removal of oxygen and/or hydrogen peroxide from an aqueous solution or another fluid matrix.

The following examples are intended to further illustrate and explain the present invention. This invention, therefore, should not be limited to any of the details in these examples.

EXAMPLE 1

A particulate carbon catalyst designated MC-10 (8 g) prepared in accordance with Chou, U.S. Pat. No. 4,696,772, and iron (III) chloride complexed with tetraphenylporphyrin (FeTPP) (2 g) were stirred into acetone (400 ml) with continued stirring for 48 hours. The solids were separated from the slurry by filtration and the filtered solids pyrolyzed at 800° C. for 2 hours under a constant flow of argon. Metal analysis of the pyrolysis product revealed that the Fe content of the solids was 1.1% by weight.

A sample (5 mg) of the Fe/N/carbon pyrolysis product designated FeTPP/MC-10 was suspended in a solution of 0.1 M orthophosphoric acid (100 ml) at 70° C. and the suspension subjected to cyclic voltammetry in the reduction of molecular oxygen using a Model 273A potentiostat/galvanostat (Princeton Applied Research, Oak Ridge, Tenn.). The applied potential was varied from 0.5 to 0.1 volts vs. an Ag/AgCl electrode immersed in the suspension. The cyclic voltammetry cell included a second electrode comprising a carbon cloth against which the suspended FeTPP/MC-10 particulates were held by circulating the solution of orthophosphoric acid through the cloth. Oxygen was bubbled into the suspension so that it gently contacted the carbon cloth electrode. As a control, a sample of unmodified MC-10 particulate carbon catalyst was subjected to cyclic voltammetry under identical conditions. The resulting voltammograms are set forth in FIG. 1.

In evaluating these results, it may be noted that, with 5 mg catalyst, a current of 105 mA is equivalent to a complete 6 electron oxidation of N-(phosphonomethyl)iminodiacetic acid at a rate 30 g N-(phosphonomethyl)iminodiacetic acid substrate/hour-gram catalyst.

Since the MC-10 particulate carbon catalyst has been used commercially for the oxidation of N-(phosphonomethyl)iminodiacetic acid to N-(phosphonomethyl)glycine, it provides a reasonable control for evaluating the oxygen reduction capability of the FeTPP/MC-10 catalyst of the invention prepared by pyrolysis of FeTPP on MC-10. While the cyclic voltammograms reflect some oxygen reduction capability of the MC-10 catalyst, radical improvement is obtained with the FeTPP/MC-10 catalyst produced in accordance with the invention.

EXAMPLE 2

Figure 2:
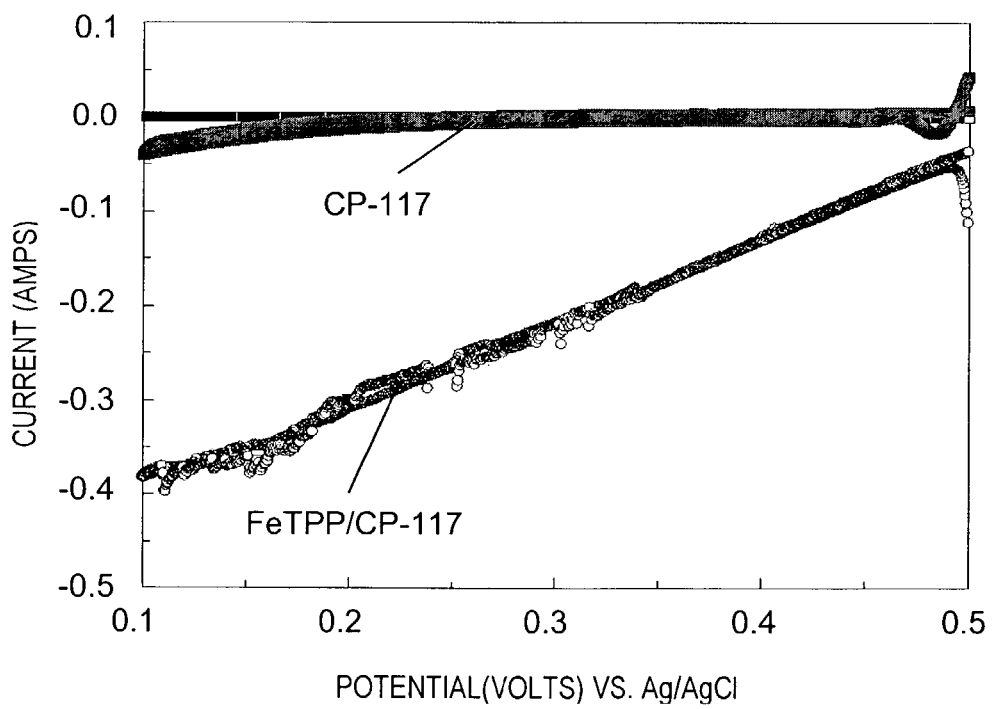
FIG. 2 shows cyclic voltammograms for the reduction of molecular oxygen as obtained in accordance with the procedure of Example 2 comparing a particulate carbon support sold under the trade designation CP-117 (Engelhard Corp., Iselin, N.J.) with a particulate carbon catalyst of the invention prepared by pyrolysis of FeTPP on a CP-117 carbon support and designated FeTPP/CP-117.

A second Fe/N/carbon catalyst in accordance with the present invention was prepared as described in Example 1 except that a particulate carbon support sold under the trade designation CP-117 (Engelhard Corp., Iselin, N.J.) was substituted for the MC-10 particulate carbon catalyst. The modified CP-117 carbon designated FeTPP/CP-117 was subjected to cyclic voltammetry in the reduction of molecular oxygen in the manner described in Example 1. Again a control was run using unmodified CP-117. The results are set forth in FIG. 2. Note that although the unmodified CP-117 carbon support is much less active with respect to oxygen reduction than is the MC-10 particulate carbon catalyst, FeTPP/CP-117 resulting from treatment of CP-117 with FeTPP and pyrolysis is nevertheless quite effective for the purpose.

EXAMPLE 3

Figure 3:
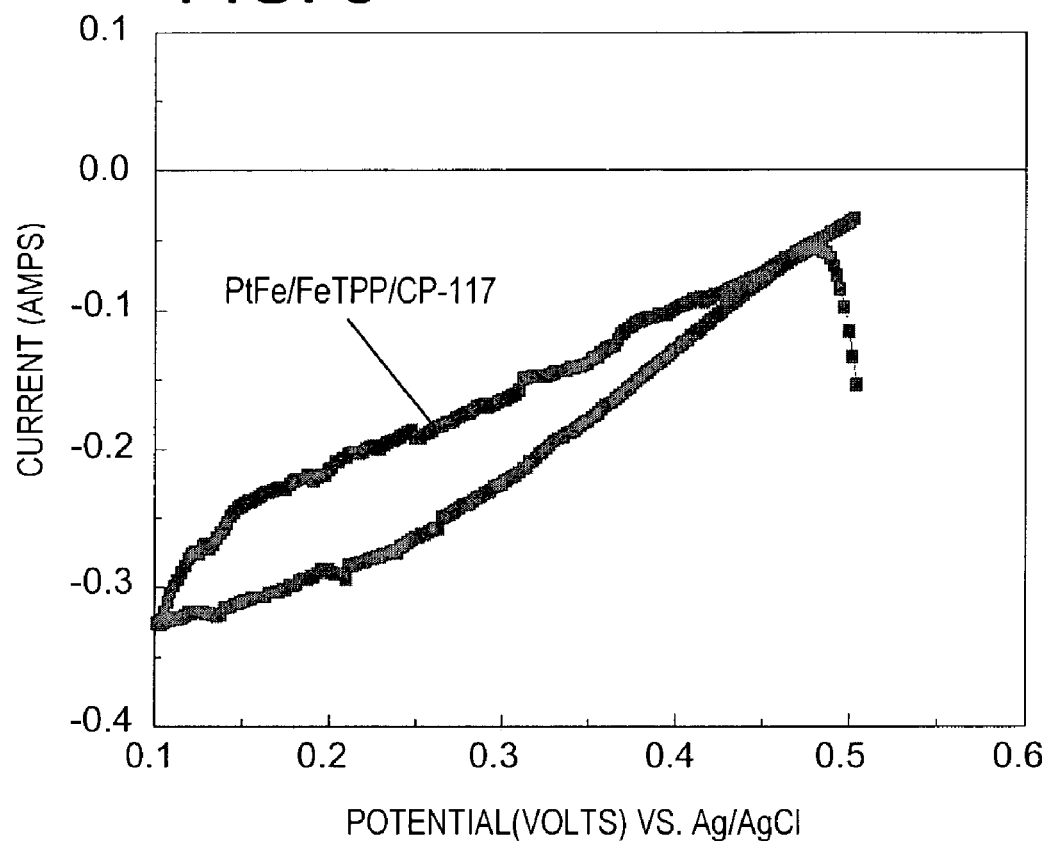
FIG. 3 shows a cyclic voltammogram for the reduction of molecular oxygen as obtained in accordance with the procedure of Example 3 for a catalyst designated PtFe/FeTPP/CP-117 prepared by depositing platinum and an iron promoter over a FeTPP/CP-117 modified carbon support prepared in accordance with Example 2.

A third Fe/N/carbon catalyst was prepared by depositing platinum (5% by weight) and an iron promoter (0.5% by weight) on the FeTPP/CP-117 modified carbon prepared in Example 2. Deposition of the Pt active phase and the Fe promoter was carried out in the manner described in U.S. Pat. No. 6,417,133. This catalyst, designated PtFe/FeTPP/CP-117, was also subjected to cyclic voltammetry in the reduction of molecular oxygen in the manner described in Example 1. The results are shown in FIG. 3.

EXAMPLE 4

Comparative oxidation runs were conducted in which the FeTPP/MC-10 modified particulate carbon catalyst prepared in Example 1 and unmodified MC-10 particulate carbon catalyst were separately tested in catalyzing the oxidation of N-(phosphonomethyl)iminodiacetic acid to N-(phosphonomethyl)glycine. In each oxidation run, a 12% by weight solution of N-(phosphonomethyl)iminodiacetic acid (60 g) in water (440 ml) was charged to a 1 liter Parr reactor together with catalyst at a loading of 0.25% (1.25 g). The mixture was heated to 100° C. and potential observed with an ORP probe. A flow of molecular oxygen gas was introduced into the mixture and the concentration of $CO_2$ in the reactor off-gas was also measured to determine the rate of oxidation. Periodic samples of the reaction mixture were taken and analyzed by high performance liquid chromatography (HPLC) for N-(phosphonomethyl)iminodiacetic acid (PMIDA), N-(phosphonomethyl)glycine (glyphosate), formaldehyde ($CH_2O$), formic acid ($HCO_2H$) and various impurities, including aminomethylphosphonic acid (AMPA)+N-methylaminomethylphosphonic acid (MAMPA), N-methyl-N-(phosphonomethyl)glycine (NMG), phosphate ion ($PO_4$) and imino-bis-(methylene)-bis-phosphonic acid (iminobis). The results of the HPLC analyses are set forth below in Table 1 for the oxidation run using the unmodified MC-10 particulate carbon catalyst, and in Table 2 for the oxidation run using the FeTPP/MC-10 modified carbon catalyst. Comparative ORP and % $CO_2$ profiles or illustrated in FIG. 4, and comparative impurity profiles plotted in FIG. 5.

TABLE 1

HPLC Analysis of PMIDA Oxidation Using Unmodified MC-10 Particulate Carbon Catalyst

| Experiment | 1A | 1B | 1C |
|---|---|---|---|
| Sample Time (minutes) | 10 | 36 | 42 |
| GLYPHOSATE % | 1.853 | 6.13 | 6.321 |
| PMIDA % | 4.508 | 0.71 | 0.00222 |
| $CH_2O$ % | 0.286 | 0.876 | 0.931 |
| $HCO_2H$ % | 0.075 | 0.443 | 0.501 |
| AMPA/MAMPA % | 0.060 | 0.119 | 0.272 |
| NMG % | 0.003 | 0.075 | 0.060 |
| $PO_4$ % | 0.010 | 0.020 | 0.025 |
| IMINOBIS % | 0.028 | 0.037 | 0.037 |

TABLE 2

HPLC Analysis of PMIDA Oxidation Using FeTPP/MC-10 Modified Particulate Carbon Catalyst

| Experiment | 2A | 2B | 2C | 2D |
|---|---|---|---|---|
| Sample Time (minutes) | Pre-heatup | 8 | 16 | 22 |
| GLYPHOSATE % | 0.299 | 3.449 | 6.79 | 6.141 |
| PMIDA % | 0.6244 | 4.414 | 0.348 | 0.00328 |
| $CH_2O$ % | 0.016 | 0.623 | 1.215 | 1.287 |
| $HCO_2H$ % | 0.025 | 0.062 | 0.162 | 0.174 |
| ANPA/MAMPA % | 0.010 | 0.006 | 0.032 | 0.438 |
| NMG % | 0.002 | 0.005 | 0.043 | 0.039 |
| $PO_4$ % | DBNQ | 0.003 | 0.006 | 0.011 |
| IMINOBIS % | 0.003 | 0.038 | 0.041 | 0.048 |

Figure 4:
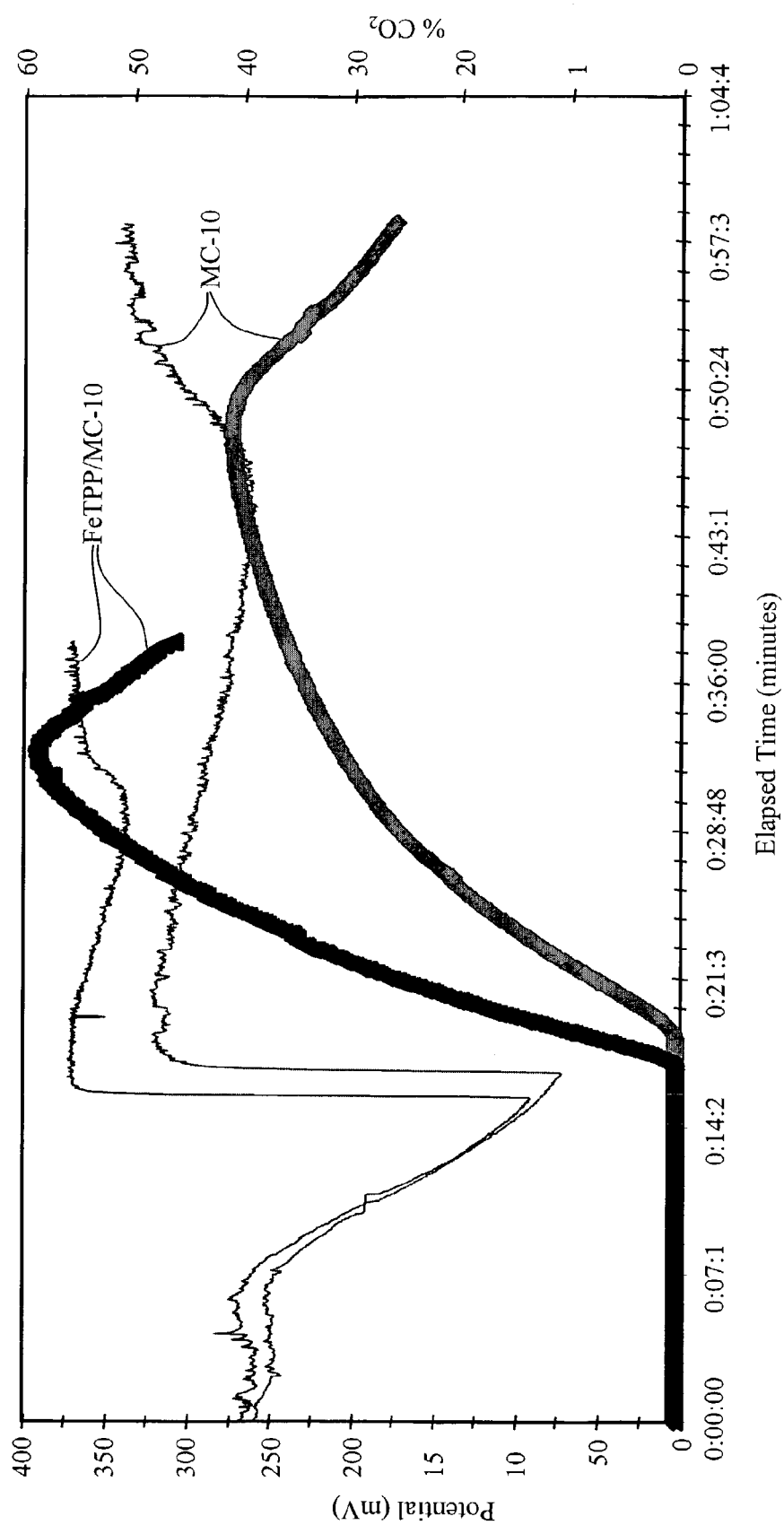
FIG. 4 sets forth the comparative profiles of ORP and % $CO_2$ in the off-gas for the oxidation runs conducted in Example 4 using the FeTPP/MC-10 modified particulate carbon catalyst prepared in Example 1 and unmodified MC-10 particulate carbon catalyst to catalyze the oxidation of N-(phosphonomethyl)iminodiacetic acid to N-(phosphonomethyl)glycine.
Figure 5:
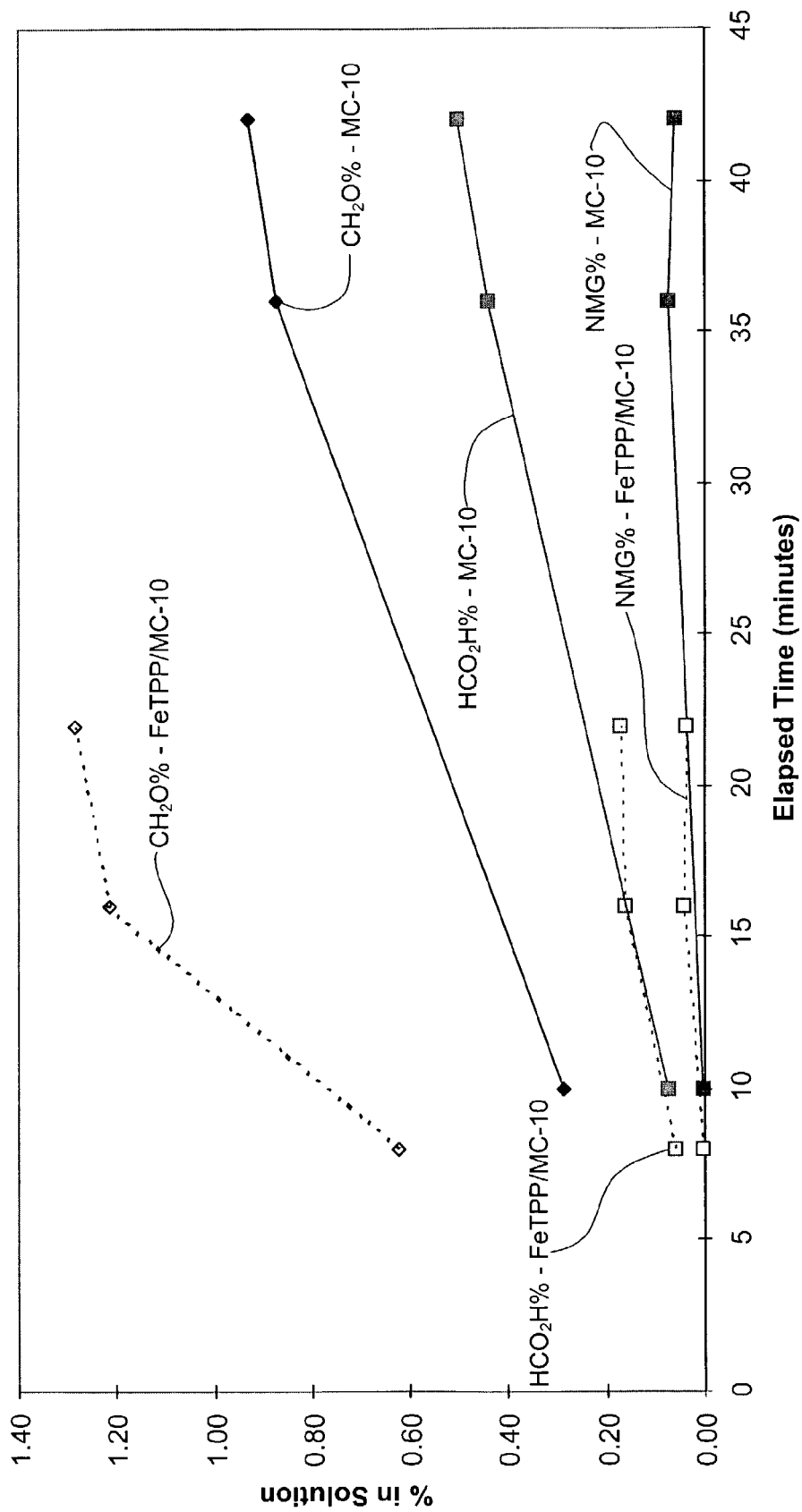
FIG. 5 plots profiles of impurities as determined by high performance liquid chromatography (HPLC) analysis of samples of reaction mixture taken during the course of the comparative oxidation runs of Example 4.

Based on the $CO_2$ evolution curve of FIG. 4, the rate of N-(phosphonomethyl)iminodiacetic acid oxidation was approximately twice as fast for the FeTPP/MC-10 modified carbon catalyst than for the unmodified MC-10 carbon catalyst. This is confirmed by the data of Tables 1 and 2. The data of Tables 1 and 2 also demonstrate that the FeTPP/MC-10 modified carbon catalyst also changed the formaldehyde to formic acid ratios significantly. Although the FeTPP/MC-10 modified catalyst produced higher formaldehyde levels than the unmodified MC-10 carbon catalyst, the amount of formic acid produced was only about half that produced using the unmodified MC-10 carbon catalyst. The level of N-methyl-N-(phosphonomethyl)glycine impurity was lower using the modified FeTPP/MC-10 carbon catalyst, possibly due to the low formic acid to formaldehyde ratio and the shorter run time.

EXAMPLE 5

Figure 6:
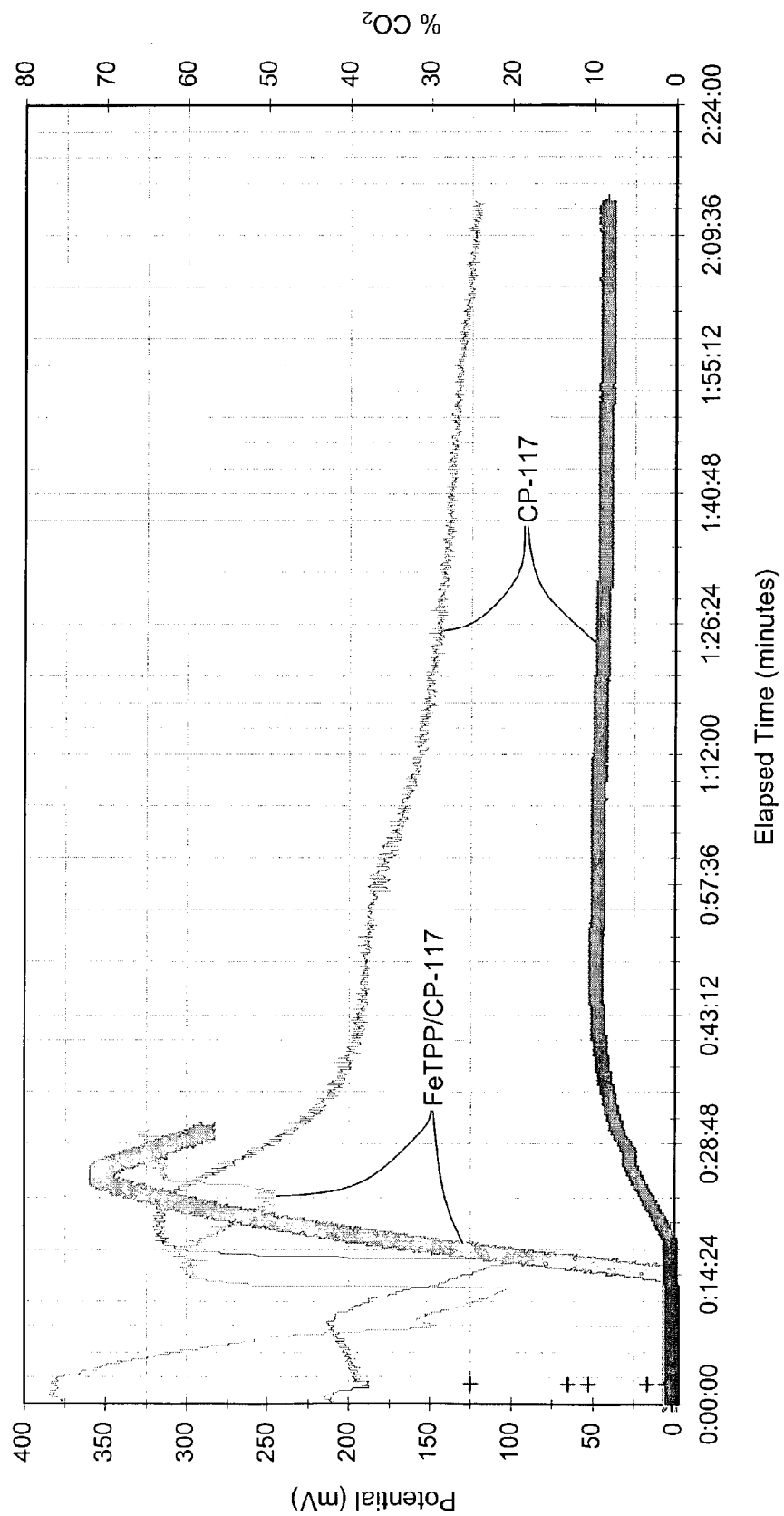
FIG. 6 sets forth the comparative profiles of ORP and % $CO_2$ in the off-gas for the oxidation runs conducted in Example 5 using the FeTPP/CP-117 modified particulate carbon catalyst prepared in Example 2 and unmodified CP-117 particulate carbon catalyst to catalyze the oxidation of N-(phosphonomethyl)iminodiacetic acid to N-(phosphonomethyl)glycine.
Figure 7:
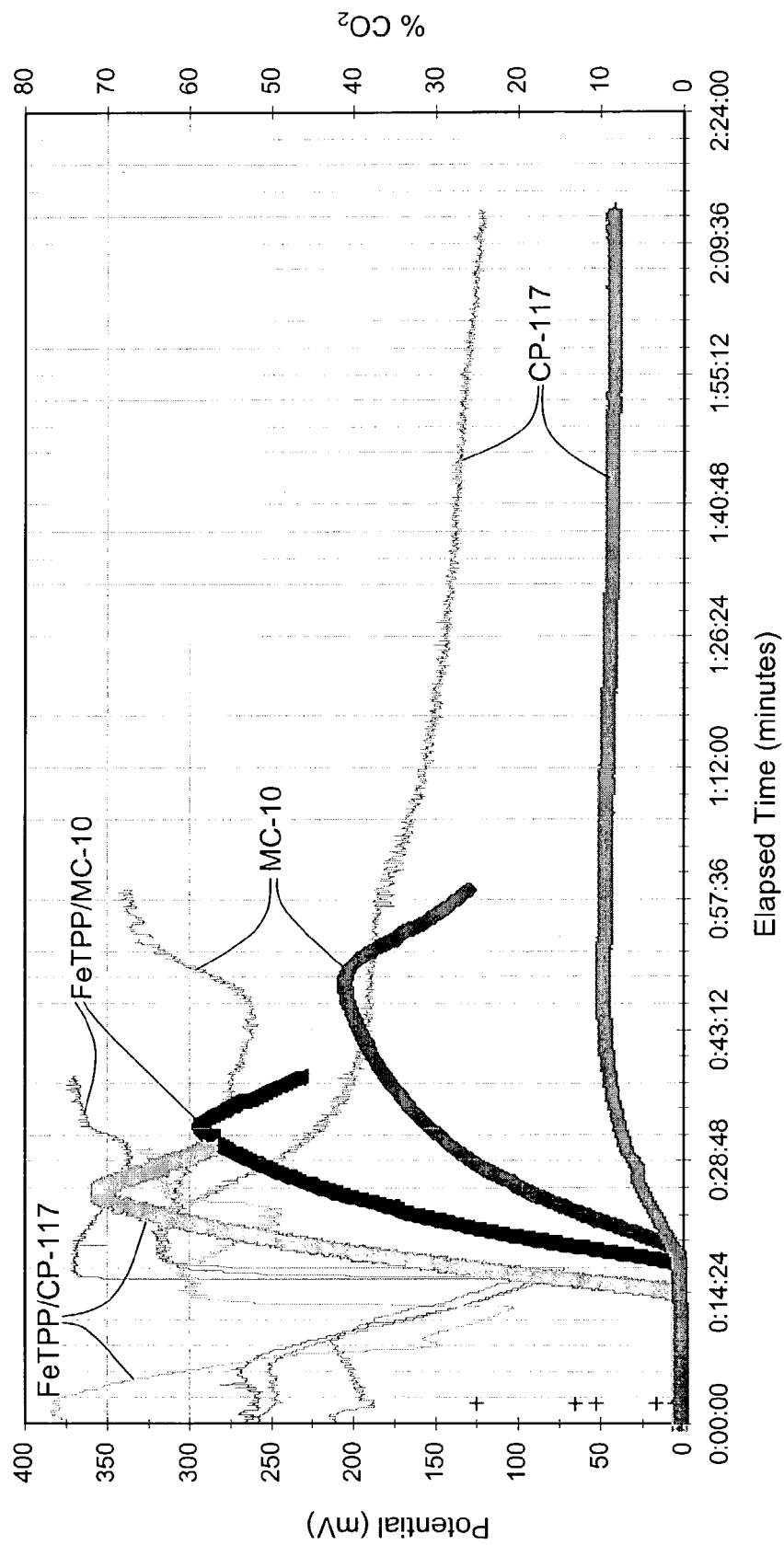
FIG. 7 constitutes an overlay of the ORP and % $CO_2$ profiles of FIG. 4 and those of FIG. 6.
Figure 8:
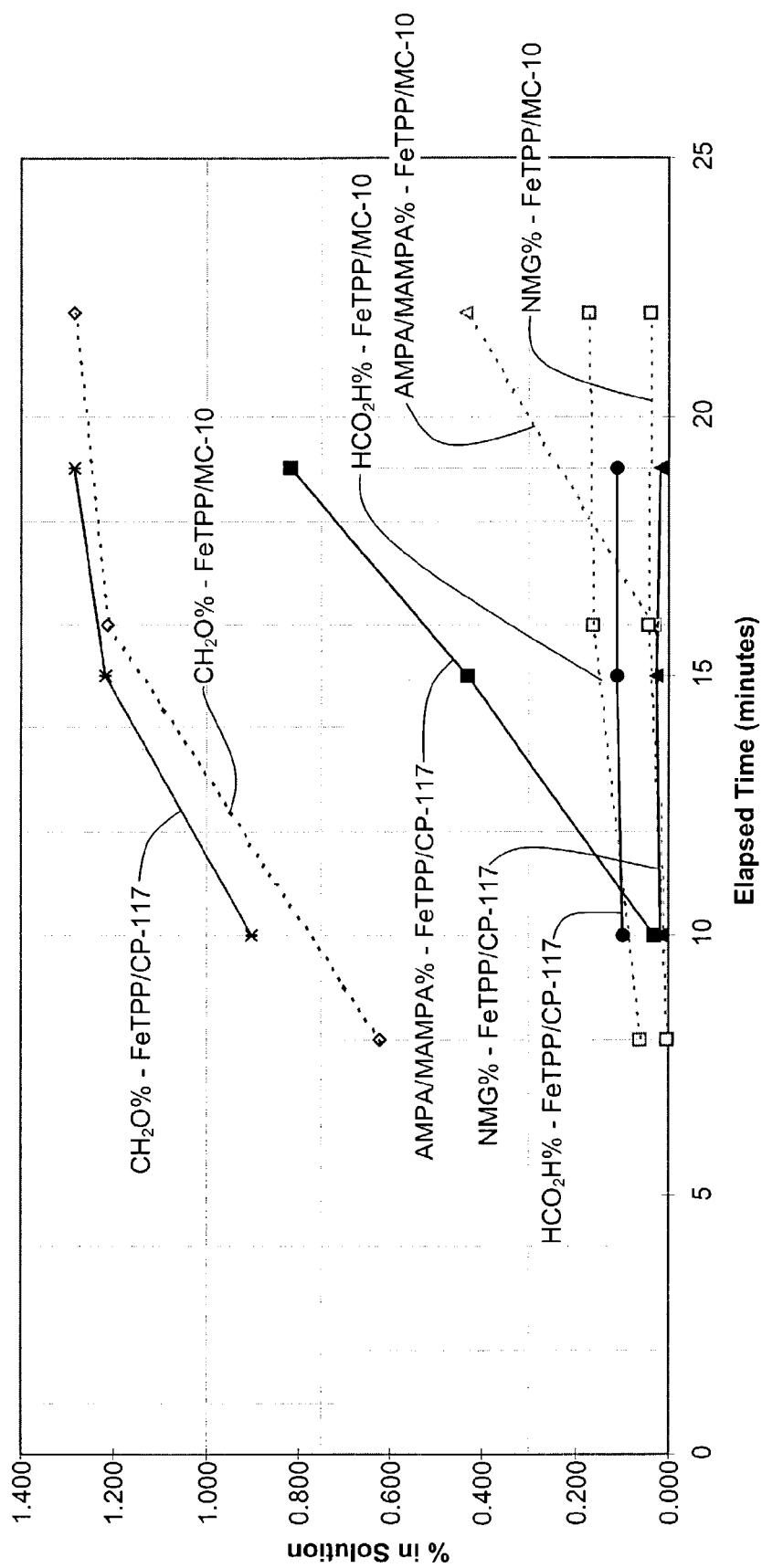
FIG. 8 is an overlay of the plot of the impurities profiles of the comparative oxidation runs of Example 4, as taken from FIG. 5, with the impurities profiles of the comparative oxidation runs of Example 5.

Comparative oxidation runs were conducted in the manner described in Example 4 except that the catalysts used were the FeTPP/CP-117 modified particulate carbon catalyst prepared in Example 2 and unmodified CP-117. HPLC analysis results are shown in Tables 3 and 4 below. Comparative $CO_2$ and ORP profiles are illustrated in FIG. 6. FIG. 7 constitutes an overlay of the data plotted in FIG. 4 from Example 4 and FIG. 6. FIG. 8 is an overlay of the plot of the impurities profiles of the comparative oxidation runs of Example 4, as taken from FIG. 5, with the impurities profiles of the comparative oxidation runs of this Example.

TABLE 3

HPLC Analysis of PMIDA Oxidation Using Unmodified CP-117 Particulate Carbon Catalyst

| Experiment | 3A | 3B | 3C |
|---|---|---|---|
| Sample Time (minutes) | 12 | 182 | 210 |
| GLYPHOSATE % | 0.821 | 6.147 | 5.834 |
| PMIDA % | *Too Conc | 0.04963 | 0.00457 |
| $CH_2O$ % | 0.092 | 0.158 | 0.150 |
| $HCO_2H$ % | 0.047 | 1.410 | 1.411 |
| AMPA/MAMPA % | 0.004 | 0.100 | 0.139 |
| NMG % | 0.002 | 0.232 | 0.213 |
| $PO_4$ % | 0.004 | 0.087 | 0.088 |
| IMINOBIS % | 0.018 | 0.033 | 0.032 |

TABLE 4

HPLC Analysis of PMIDA Oxidation Using FeTPP/CP-117 Modified Particulate Carbon Catalyst

| Experiment | 4A | 4B | 4C |
|---|---|---|---|
| Sample Time (minutes) | 10 | 15 | 19 |
| GLYPHOSATE % | 5.639 | 6.401 | 5.73 |
| PMIDA % | 1.442 | 0.02187 | 0.00226 |
| $CH_2O$ % | 0.899 | 1.219 | 1.285 |
| $HCO_2H$ % | 0.096 | 0.109 | 0.109 |
| AMPA/MAMPA % | 0.030 | 0.434 | 0.815 |
| NMG % | 0.019 | 0.025 | 0.016 |
| $PO_4$ % | 0.003 | 0.004 | 0.006 |
| IMINOBIS % | 0.048 | 0.052 | 0.053 |

As shown in FIG. 8 and in Table 4, the impurities profiles for the FeTPP/CP-117 modified carbon catalyst are very similar to those for the FeTPP/MC-10 modified carbon catalyst, especially with regard to formaldehyde, formic acid and N-methyl-N-(phosphonomethyl)glycine. A difference does in appear in the levels of aminomethylphosphonic acid (AMPA)+N-methylaminomethylphosphonic acid (MAMPA) in the reaction solution. It appears that the oxidation reaction using the FeTPP/CP-117 modified carbon catalyst was so fast that the N-(phosphonomethyl)glycine product was exposed to oxidation before the reaction cycle was terminated.

EXAMPLE 6

Figure 9:
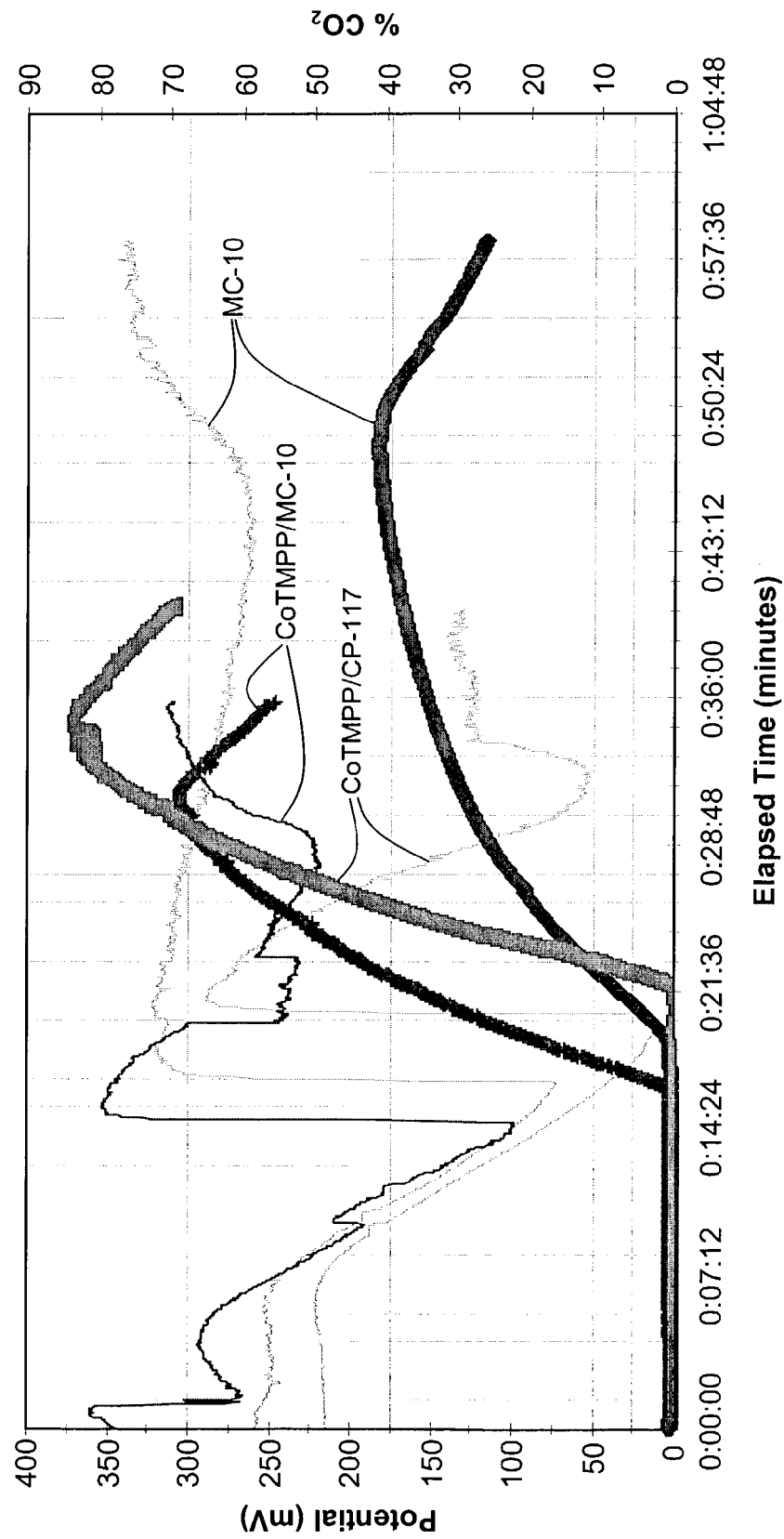
FIG. 9 sets forth the comparative profiles of ORP and % $CO_2$ in the off-gas for the oxidation runs conducted in Example 6 using the CoTMPP/MC-10 and CoTMPP/CP-117 modified particulate carbon catalysts and unmodified MC-10 carbon catalyst to catalyze the oxidation of N-(phosphonomethyl)iminodiacetic acid to N-(phosphonomethyl)glycine.

Transition metal/N on carbon catalyst were prepared by treatment of MC-10 and CP-117 carbons with a co-ordination complex and pyrolysis substantially in the manner described as described in Examples 1 and 2 except that cobalt rather than iron was used as the transition metal and tetramethoxyphenyl porphyrin (TMPP) served as the ligand in the coordination complex. Comparative N-(phosphonomethyl)iminodiacetic acid oxidation runs were conducted using separately the modified carbon catalyst, designated CoTMPP/MC-10 and CoTMPP/CP-117, and unmodified MC-10 particulate carbon catalyst substantially in the manner as described in Examples 4 and 5. Comparative ORP and % $CO_2$ in the off gas profiles are plotted in FIG. 9.

EXAMPLE 7

Figure 10:
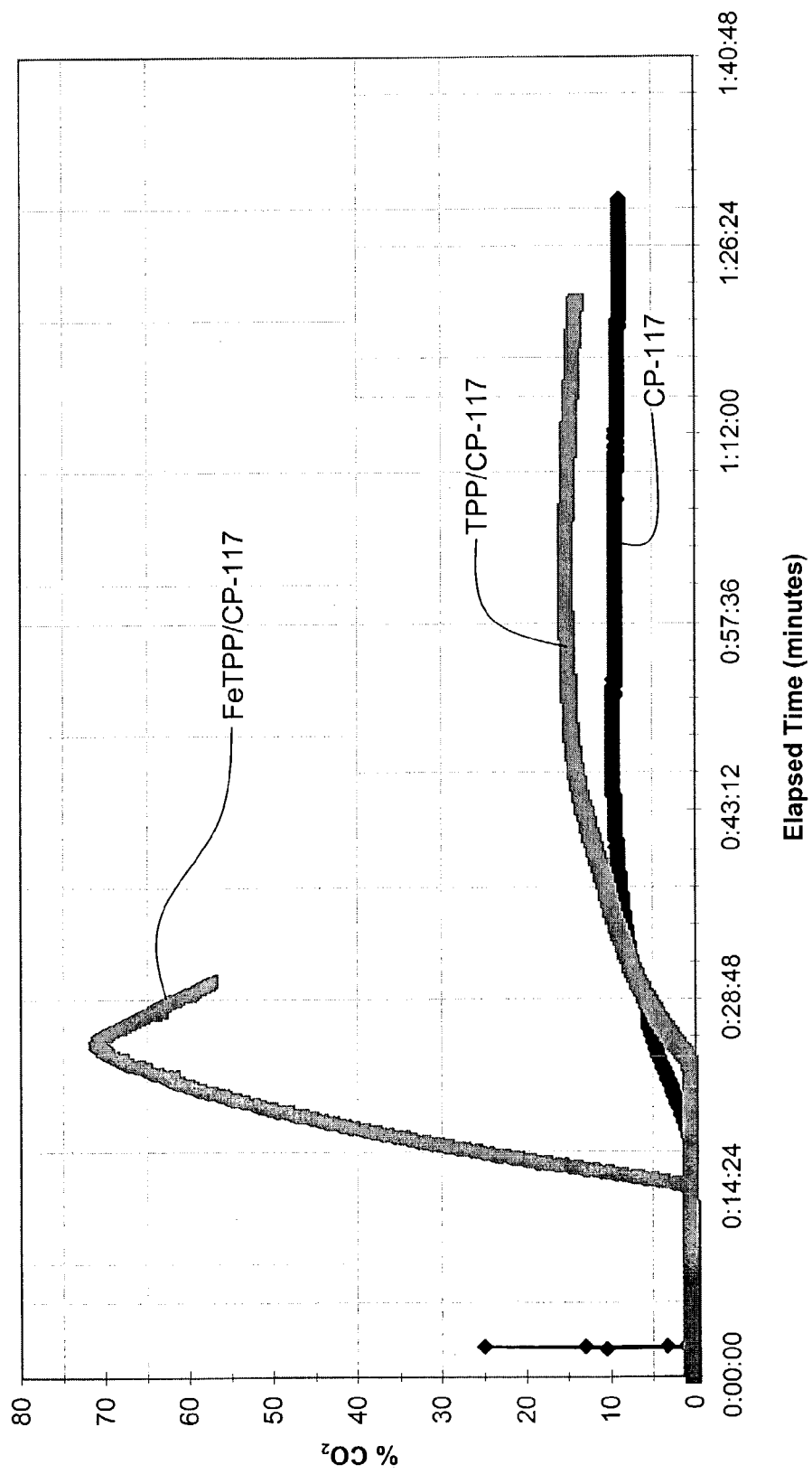
FIG. 10 sets forth the comparative profiles of % $CO_2$ in the off-gas for the oxidation runs conducted in Example 7 using the TPP/CP-117 and FeTPP/CP-117 modified particulate carbon catalysts and unmodified CP-117 particulate carbon catalyst to catalyze the oxidation of N-(phosphonomethyl)iminodiacetic acid to N-(phosphonomethyl)glycine.

A modified CP-117 carbon catalyst was prepared in the manner described in Example 2 except that only TPP, not a transition metal/TPP complex, was deposited on the carbon surface prior to pyrolysis at 800° C. Comparative N-(phosphonomethyl)iminodiacetic acid oxidation runs were conducted comparing the performance of this catalyst, designated TPP/CP-117, with the FeTPP/CP-117 modified catalyst of Example 2 and a control in which unmodified CP-117 particulate carbon catalyst was used. These runs were conducted substantially in the manner as described in Example 4. Comparative % $CO_2$ in the off gas profiles are plotted in FIG. 10.

EXAMPLE 8

Figure 11:
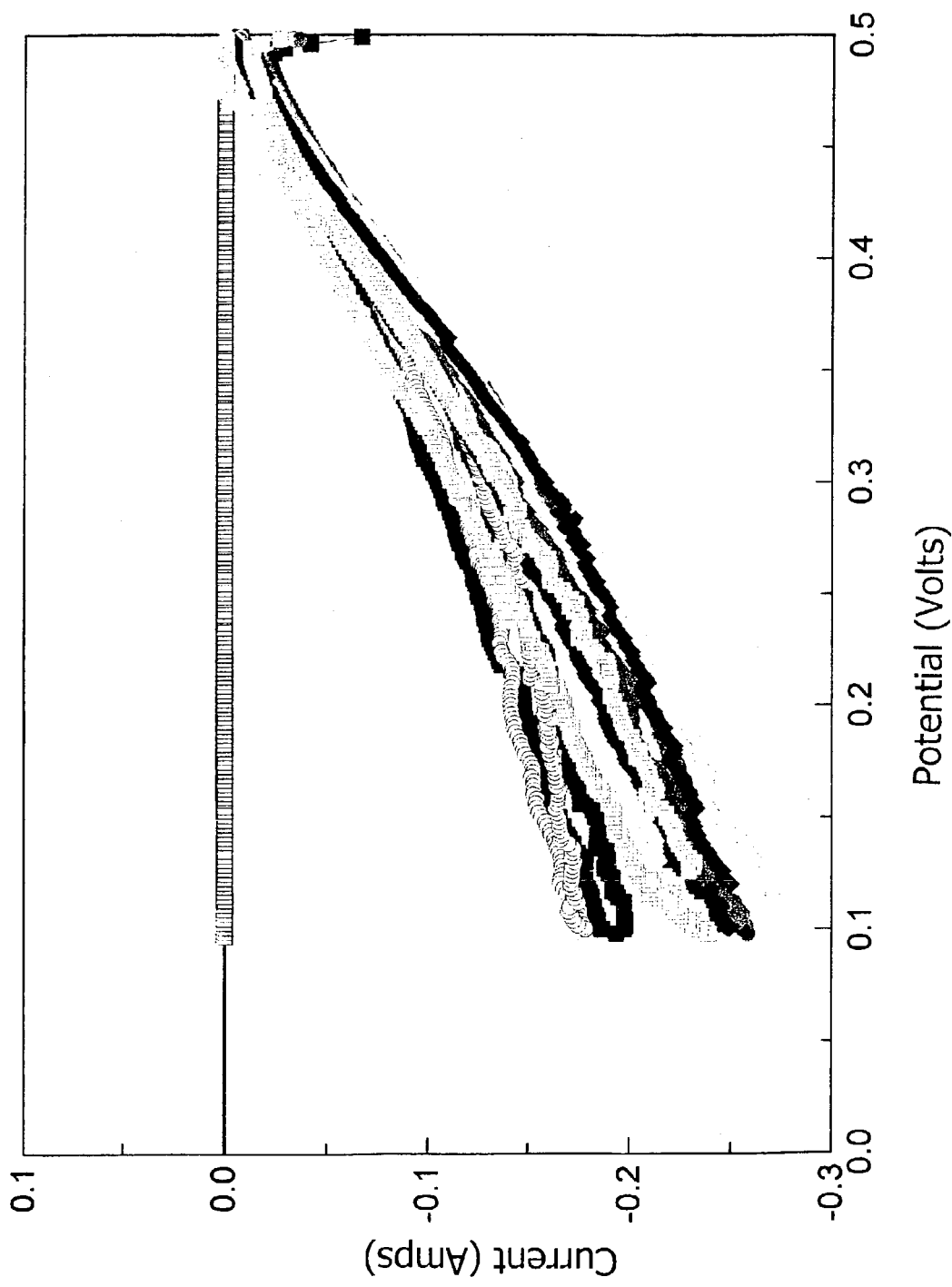
FIG. 11 shows cyclic voltammograms for the reduction of molecular oxygen as obtained in accordance with the procedure of Example 8 for a hydrochloric acid washed FeTPP-117/CP-117 modified particulate carbon catalyst.

An FeTPP/CP-117 modified catalyst in accordance with the present invention was prepared substantially in the manner described in Example 2 above. The catalyst was washed in 0.2% by weight hydrochloric acid (HCl). Metal analyses conducted before and after the acid wash indicated a metal loss of 62 to 75%. Subsequent to acid washing, the FeTPP/CP-117 modified catalyst was subjected to cyclic voltammetry in the reduction of molecular oxygen using the method described in Example 1 at a pH of 1.91. The voltammograms resulting from repeated sweeps are set forth in FIG. 11. The electrochemical data show good current for oxygen reduction for the acid washed catalyst, between 175 and 275 mA. While the acid wash resulted in a substantial loss of Fe, the acid washed FeTPP/CP-117 modified catalyst did not suffer a proportionate loss in activity for oxygen reduction when compared to the electrochemical data generated by subjecting the FeTPP/CP-117 modified catalyst to cyclic voltammetry before acid washing.

EXAMPLE 9

Figure 12:
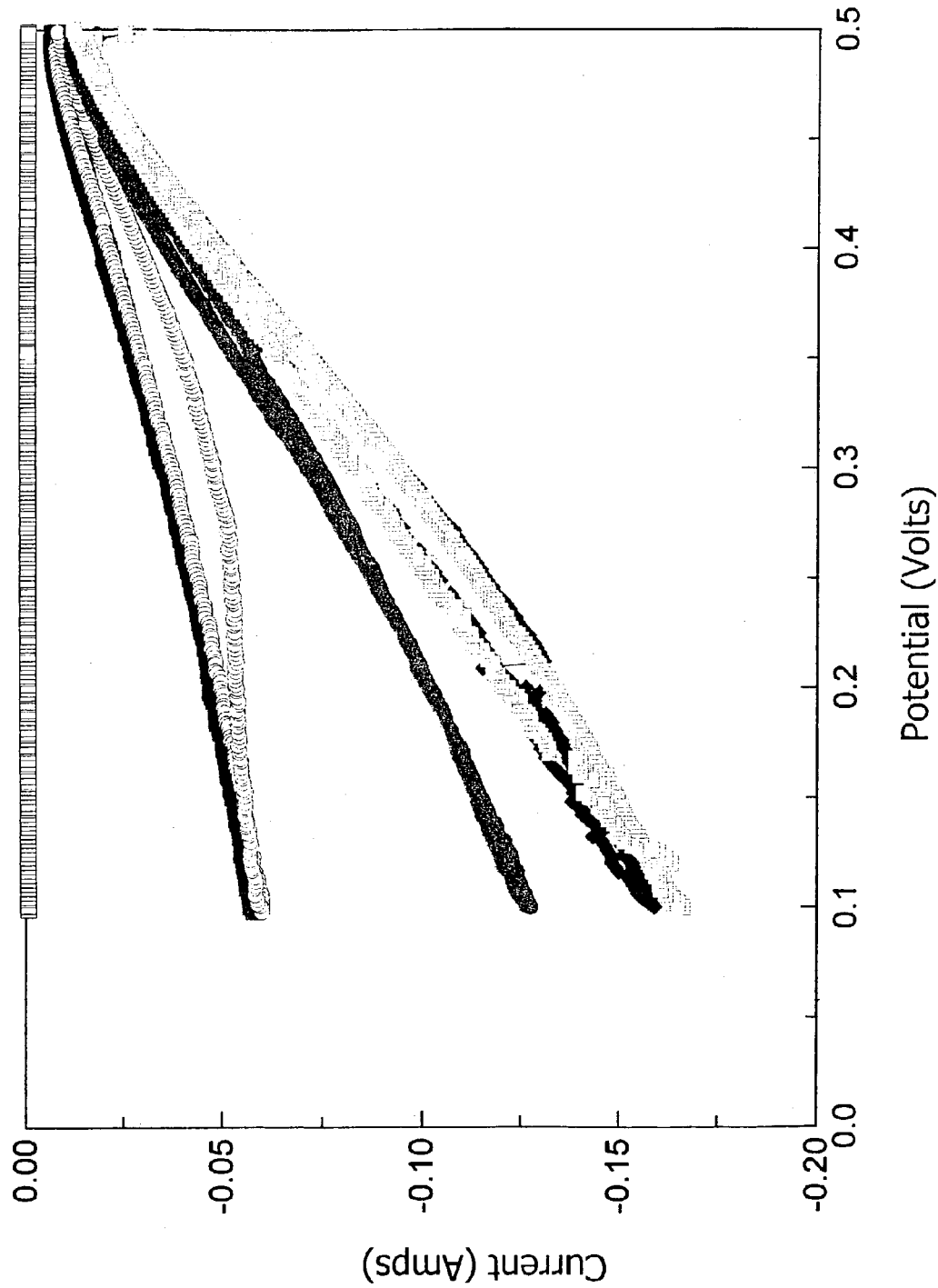
FIG. 12 shows cyclic voltammograms for the reduction of molecular oxygen as obtained in accordance with the procedure of Example 9 for a hydrochloric acid washed PtFe/FeTPP-117/CP-117 modified particulate carbon catalyst.

An iron-promoted platinum on carbon catalyst containing 5% by weight Pt and 0.5% by weight Fe promoter was prepared by depositing Pt and Fe onto an FeTPP/CP-117 modified carbon prepared in the manner of Example 2. The catalyst was washed in 0.2% by weight hydrochloric acid (HCl). The metal loadings changed from 5.0% Pt and 1.9% Fe before acid washing to 3.7% Pt and 1.2% Fe after acid washing, again indicating a substantial loss of metal. Subsequent to acid washing, the PtFe/FeTPP/CP-117 modified catalyst was subjected to cyclic voltammetry in the reduction of molecular oxygen using the method described in Example 1 at a pH of 1.92. The voltammograms resulting from repeated sweeps are set forth in FIG. 12. The electrochemical data show a modest $O_2$ reduction current of 50 mA for the first two cycles that rise to 175 mA in subsequent cycles.

EXAMPLE 10

MC-10 particulate carbon catalyst prepared in accordance with Chou, U.S. Pat. No. 4,696,772, was modified by providing an Fe/N composition on the carbon bodies in accordance with the method generally described in Example 1. Using the noble metal on carbon catalyst preparation method described hereinabove and in U.S. Pat. No. 6,417, 133, platinum and an iron promoter were deposited on the modified MC-10 carbon support. The Fe-promoted Pt on Fe/N modified carbon catalyst contained about 5% by weight noble metal and about 0.5% by weight Fe promoter. After Pt and Fe deposition, the catalyst was pyrolyzed at 800° C. in 7% $H_2$ in Argon for 2 hours.

A portion of the pyrolyzed Pt/Fe on modified carbon catalyst (1.38 g) and an aqueous solution (448 ml) containing N-(phosphonomethyl)iminodiacetic acid (PMIDA) (50 g; 10% by weight) was charged to a 1 liter reactor. The charge mixture was heated to 100° C. under nitrogen, after which molecular oxygen gas was introduced into the mixture at a rate of 2.111 g moles/kg-hr. The reaction mass was sampled at 6 minutes, 10 minutes, 15 minutes, 19 minutes and 22 minutes after the start of oxygen flow. Each of these samples was analyzed for N-(phosphonomethyl)glycine (glyphosate), N-(phosphonomethyl)iminodiacetic acid (PMIDA), formaldehyde ($CH_2O$), formic acid ($HCO_2H$), N-methyl-N-phosphonomethyl(glycine) (NMG), phosphate ion ($PO_4$) and aminomethylphosphonic acid (AMPA)+N-methylaminomethylphosphonic acid (MAMPA).

From the analytical data, computations were made of the total $C_1$ compounds generated between successive pairs of samples, total $C_1$ compounds oxidized between samples, formic acid oxidized between samples, formaldehyde oxidized between samples, total oxygen demand between samples, average rate of oxygen consumption between samples, average rate of oxidation of N-(phosphonomethyl) iminodiacetic acid between samples, average rate of formaldehyde oxidation between samples, average proportion of $CO_2$ in the off gas from the reactor during operation between samples, integrated average Arrhenius constant for oxidation of formaldehyde between samples, and integrated average Arrhenius constant for oxidation of formic acid between samples. The results are set forth in Table 5, which also includes a computation of the phosphorus and nitrogen material balance closure between the second (10 minute) and third (15 minute) samples, and between the third and fourth (19 minute) samples.

TABLE 5

| Averages for | 0-Smp 1 6 min | Smp 1–2 10 min | Smp 2–3 15 min | Smp 3–4 19 min | Smp 4–5 22 min | Smp 5–6 min | Smp 6–7 min | Up to ~EP 19 min |
|---|---|---|---|---|---|---|---|---|
| $C_1$'s ox./$C_1$'s gen (%) | 43.01 | 36.03 | 59.32 | 89.33 | 88086.24 | — | — | 56.34 |
| $HCO_2H$ ox/$CH_2O$ ox (%) | 65.79 | 62.38 | 76.33 | 89.13 | 141.31 | — | — | 75.56 |
| Total $O_2$ req'd (gmoles/hr) | 0.80 | 0.52 | 0.83 | 0.83 | 0.29 | — | — | 0.78 |
| $rO_2$ (gmoles/kgm-hr) | 1.60 | 1.04 | 1.65 | 1.66 | 0.58 | — | — | 1.56 |
| r(PMIDA) (gmoles/kgm-hr) | 1.53 | 1.08 | 1.39 | 1.14 | 0.00 | — | 0.00 | 1.36 |
| r($CH_2O$) (gmoles/kgm-hr) | 1.00 | 0.62 | 1.08 | 1.14 | 0.46 | — | — | 1.01 |
| r($HCO_2H$) (gmoles/kgm-hr) | 0.6 | 0.39 | 0.83 | 1.02 | 0.66 | — | — | 0.76 |
| $CO_2$ Calc (% in off gas) | 81.11% | 57.94% | 82.96% | 82.65% | 30.12% | — | — | 79.52% |
| k($CH_2O$) (1/hr) | 28.1928 | 8.4980 | 10.7479 | 10.4666 | 4.9688 | — | — | 9.2529 |
| k($HCO_2H$) (1/hr) | 28.6996 | 9.6943 | 12.8734 | 13.2620 | 8.9875 | — | — | 9.7643 |
| P & N balance (Out/In) | | | 97.5989 | 97.8332 | 95.2785 | — | — | 95.3597 |

EXAMPLE 11

Using a catalyst prepared in the manner described in Example 10, oxidation of N-(phosphonomethyl)iminodiacetic acid to N-(phosphonomethyl)glycine was conducted in the manner also described in Example 10 except that the aqueous charge solution contained N-(phosphonomethyl)iminodiacetic acid in the amount of 60 g (12% by weight) rather than 50 g (10% by weight). Sampling and calculations were carried out in the manner described in Example 10, providing the results summarized in Table 6.

EXAMPLE 12

N-(phosphonomethyl)iminodiacetic acid was oxidized to N-(phosphonomethyl)glycine using the process as described in Example 11. The catalyst was prepared in the manner described in Example 10, except that final pyrolysis was conducted at 850° C. rather than 800° C. Sampling and calculations were carried out in the manner described in Example 10, providing the results summarized in Table 7.

TABLE 6

| Averages for | 0-Smp 1 5 min | Smp 1–2 10 min | Smp 2–3 15 min | Smp 3–4 20 min | Smp 4–5 27 min | Smp 5–6 min | Smp 6–7 min | Up to ~EP 24 min |
|---|---|---|---|---|---|---|---|---|
| $C_1$'s ox./$C_1$'s gen (%) | 31.48 | 39.66 | 57.10 | 84.30 | 267.18 | — | — | 56.19 |
| $HCO_2H$ ox/$CH_2O$ ox (%) | 60.48 | 61.14 | 72.65 | 90.84 | 113.71 | — | — | 75.68 |
| Total $O_2$ req'd (gmoles/hr) | 0.72 | 0.73 | 0.87 | 0.95 | 0.40 | — | — | 0.74 |
| r($O_2$) (gmoles/kgm-hr) | 1.45 | 1.47 | 1.75 | 1.90 | 0.81 | — | — | 1.49 |
| r(PMIDA) (gmoles/kgm-hr) | 1.57 | 1.43 | 1.48 | 1.37 | 0.26 | — | 0.00 | 1.29 |
| r($CH_2O$) (gmoles/kgm-hr) | 0.82 | 0.93 | 1.16 | 1.27 | 0.61 | — | — | 0.96 |
| r($HCO_2H$) (gmoles/kgm-hr) | 0.50 | 0.57 | 0.84 | 1.15 | 0.69 | — | — | 0.73 |
| $CO_2$ Calc (% in off gas) | 75.67% | 75.71% | 86.47% | 92.20% | 42.15% | — | — | 76.49% |
| k($CH_2O$) (1/hr) | 19.4494 | 10.2145 | 9.4947 | 9.2816 | 5.4317 | — | — | 7.2092 |
| k($HCO_2H$) (1/hr) | 27.4077 | 12.0496 | 11.2915 | 12.7952 | 7.9788 | — | — | 7.7793 |
| P & N balance (Out/In) | | | 87.4567 | 101.2419 | 99.0351 | — | — | 97.4716 |

TABLE 7

| Averages for | 0-Smp 1 5 min | Smp 1–2 10 min | Smp 2–3 15 min | Smp 3–4 20 min | Smp 4–5 25 min | Smp 5–6 min | Smp 6–7 min | Up to ~EP 22 min |
|---|---|---|---|---|---|---|---|---|
| $C_1$'s ox./$C_1$'s gen (%) | 21.28 | 26.68 | 51.57 | 68.05 | 962.54 | — | — | 44.72 |
| $HCO_2H$ ox/$CH_2O$ ox (%) | 48.12 | 45.27 | 68.92 | 79.36 | 137.62 | — | — | 65.95 |
| Total $O_2$ req'd (gmoles/hr) | 0.69 | 0.76 | 0.90 | 0.81 | 0.36 | — | — | 0.75 |
| r($O_2$)(gmoles/kgm-hr) | 1.38 | 1.53 | 1.81 | 1.62 | 0.72 | — | — | 1.50 |
| r(PMIDA) (gmoles/kgm-hr) | 1.66 | 1.65 | 1.60 | 1.27 | 0.08 | — | 0.00 | 1.41 |
| r($CH_2O$) (gmoles/kgm-hr) | 0.73 | 0.97 | 1.19 | 1.09 | 0.55 | — | — | 0.96 |
| r($HCO_2H$) (gmoles/kgm-hr) | 0.35 | 0.44 | 0.82 | 0.87 | 0.75 | — | — | 0.63 |
| $CO_2$ Calc (% in off gas) | 73.29% | 78.28% | 88.95% | 81.35% | 37.37% | — | — | 76.96% |
| k($CH_2O$) (1/hr) | 14.1961 | 8.4482 | 7.6563 | 6.1607 | 3.4994 | — | — | 5.7473 |
| k($HCO_2H$) (1/hr) | 16.6133 | 7.1583 | 8.5058 | 7.2455 | 6.5757 | — | — | 5.2814 |
| P & N balance (Out/In) | | | | 102.0112 | 99.3144 | — | — | 98.3704 |

COMPARATIVE EXAMPLE A

For purposes of comparison another oxidation run was conducted in the manner described in Example 11 except that the catalyst used was unmodified MC-10 particulate carbon catalyst prepared in accordance with Chou, U.S. Pat. No. 4,696,772. Sampling and calculations were carried out in the manner described in Example 10, providing the results summarized in Table 8.

TABLE 8

| Averages for | 0-Smp 1 5 min | Smp 1–2 10 min | Smp 2–3 20 min | Smp 3–4 26 min | Smp 4–5 32 min | Smp 5–6 40 min | Smp 6–7 7 min | Up to ~EP 34 min |
|---|---|---|---|---|---|---|---|---|
| $C_1$'s ox./$C_1$'s gen (%) | 18.80 | 16.61 | 42.87 | 49.98 | 94.09 | 205.16 | — | 43.91 |
| $HCO_2H$ ox/$CH_2O$ ox (%) | 40.14 | 28.08 | 48.85 | 54.31 | 88.91 | 105.68 | — | 55.75 |
| Total $O_2$ req'd (gmoles/hr) | 0.47 | 0.53 | 0.54 | 0.50 | 0.47 | 0.28 | — | 0.51 |
| r($O_2$)(gmoles/kgm-hr) | 0.94 | 1.06 | 1.08 | 0.99 | 0.95 | 0.56 | — | 1.02 |
| r(PMIDA) (gmoles/kgm-hr) | 1.13 | 1.21 | 0.94 | 0.82 | 0.63 | 0.22 | 0.00 | 0.91 |
| r($CH_2O$) (gmoles/kgm-hr) | 0.53 | 0.71 | 0.82 | 0.75 | 0.67 | 0.42 | — | 0.72 |
| r($HCO_2H$) (gmoles/kgm-hr) | 0.21 | 0.20 | 0.40 | 0.41 | 0.59 | 0.44 | — | 0.40 |
| $CO_2$ Calc (% in off gas) | 53.43% | 57.32% | 56.59% | 52.36% | 51.23% | 29.73% | — | 54.56% |
| k($CH_2O$) (1/hr) | 15.7754 | 9.1884 | 7.9078 | 6.5684 | 5.8229 | 4.4041 | — | 6.5437 |
| k($HCO_2H$) (1/hr) | 12.0122 | 3.6380 | 3.4582 | 2.5195 | 3.3144 | 2.4715 | — | 2.2232 |
| P & N balance (Out/In) | | | | 99.7028 | 99.2844 | 100.0640 | — | 97.6328 |

Based on comparison of the results of this Example with the results achieved in the catalytic oxidation reactions of Examples 10 to 12, it is apparent that the catalyst of the invention is more effective for the reduction of oxygen than an otherwise identical catalyst wherein the carbon support has not been modified to provide a transition metal/nitrogen composition on the carbon. It may further be concluded that the catalyst of the invention comprises sites formed by the pyrolytic treatment that are especially effective for the reduction of oxygen, and that such sites comprise nitrogen, a transition metal, or a combination of nitrogen and transition metal. In the aggregate, these formed catalytic reduction sites are more active for the reduction of oxygen than the catalytic reduction sites of the carbon support prior to modification in accordance with the present invention. Indeed the modified catalyst comprises a population of reduction sites that are each more active for the reduction of oxygen than substantially any sites of the carbon support prior to modification.

The present invention is not limited to the above embodiments and can be variously modified. The above description of the preferred embodiments, including the Examples, is intended only to acquaint others skilled in the art with the invention, its principles, and its practical application so that others skilled in the art may adapt and apply the invention in its numerous forms, as may be best suited to the requirements of a particular use.

With reference to the use of the word(s) comprise or comprises or comprising in this entire specification (including the claims below), unless the context requires otherwise, those words are used on the basis and clear understanding that they are to be interpreted inclusively, rather than exclusively, and that each of those words is intended to be so interpreted in construing this entire specification.

What is claimed is:

1. A process for the oxidation of an organic substrate selected from the group consisting of carbohydrates, alcohols, aldehydes, tertiary amines, secondary amines and acids, wherein the alcohols are oxidized to aldehydes, ketones and/or acids, the aldehydes are oxidized to acids, the tertiary amines are oxidized to secondary amines, the secondary amines are oxidized to primary amines and the acids are oxidized to carbon dioxide and water, the process comprising contacting said substrate with an oxidizing agent in the presence of an oxidation catalyst, said oxidation catalyst comprising a noble metal deposited over a modified carbon support comprising a carbon support having a transition metal/nitrogen composition thereon, said transition metal/nitrogen composition comprising an iron or cobalt nitride, an iron or cobalt nitride-carbide or combinations thereof.

2. A process as set forth in claim 1 wherein said transition metal/nitrogen composition is fixed to said carbon support.

3. A process as set forth in claim 2 wherein the noble metal is selected from the group consisting of platinum, palladium, rhodium, iridium, osmium, ruthenium and mixtures thereof.

4. A process as set forth in claim 2 wherein the noble metal is platinum.

5. A process as set forth in claim 2 wherein the concentration of the noble metal deposited at the surface of the modified carbon support is from about 2.5 to about 10% by weight of said catalyst.

6. A process as set forth in claim 2 wherein said transition metal/nitrogen composition comprises an iron or cobalt nitride.

7. A process as set forth in claim 2 wherein said transition metal/nitrogen composition comprises an active phase for the catalysis of a redox reaction.

8. A process as set forth in claim 2 wherein said oxidation catalyst comprises a particulate carbon support.

9. A process as set forth in claim 8 wherein said transition metal/nitrogen composition constitutes at least about 0.2% by weight of said catalyst.

10. A process as set forth in claim 6 wherein said transition metal/nitrogen composition constitutes from about 0.4% to about 6% by weight of said catalyst.

11. A process as set forth in claim 8 wherein said catalyst comprises said transition metal/nitrogen composition in such proportion that the Fe, Co or the sum of (Fe+Co) of said transition metal/nitrogen composition constitutes at least about 0.1% by weight of said catalyst, and the nitrogen of said transition metal/nitrogen composition constitutes at least about 0.01% by weight of said catalyst.

12. A process as set forth in claim 11 wherein said catalyst comprises said transition metal/nitrogen composition in such proportion that the Fe, Co or the sum of (Fe+Co) of said transition metal/nitrogen composition constitutes from about 0.1% to about 10% by weight of said catalyst, and the nitrogen of said transition metal/nitrogen composition constitutes from about 0.01% to about 10% by weight of said catalyst.

13. A process as set forth in claim 12 wherein said catalyst comprises said transition metal/nitrogen composition in such proportion that the Fe, Co or the sum of (Fe+Co) of said transition metal/nitrogen composition constitutes from about 0.25% to about 7% by weight of said catalyst, and the nitrogen of said transition metal/nitrogen composition constitutes from about 0.1% to about 7% by weight of said catalyst.

14. A process as set forth in claim 13 wherein said catalyst comprises said transition metal/nitrogen composition in such proportion that the Fe, Co or the sum of (Fe+Co) of said transition metal/nitrogen composition constitutes from about 0.5% to about 5% by weight of said catalyst, and the nitrogen of said transition metal/nitrogen composition constitutes from about 1% to about 5% by weight of said catalyst.

15. A process as set forth in claim 12 wherein said catalyst comprises said transition metal/nitrogen composition in such proportion that the Fe, Co or the sum of (Fe+Co) of said transition metal/nitrogen composition constitutes from about 0.2% to about 3% by weight of said catalyst, and the nitrogen of said transition metal/nitrogen composition constitutes from about 0.2% to about 3% by weight of said catalyst.

16. A process as set forth in claim 12 wherein said particulate carbon support is porous and said transition metal/nitrogen composition is substantially evenly distributed throughout the carbon particle.

17. A process as set forth in claim 12 wherein said transition metal/nitrogen composition comprises an iron or cobalt nitride.

18. A process as set forth in claim 17 wherein said transition metal/nitrogen composition comprises $\xi$-$Fe_3N$.

19. A process as set forth in claim 18 wherein said transition metal/nitrogen composition further comprises an iron species selected from the group consisting of iron oxides, iron carbides, and metallic iron.

20. A process as set forth in claim 17 wherein said transition metal/nitrogen composition comprises an iron nitride and superparamagnetic iron.

21. A process as set forth in claim 20 wherein said transition metal/nitrogen composition as determined from Mössbauer spectra comprises from about 30% to about 70% by weight $\xi$-$Fe_3N$ and from about 5% to about 20% by weight superparamagnetic iron.

22. A process as set forth in claim 21 wherein said transition metal/nitrogen composition as determined from Mössbauer spectra further comprises an additional iron species selected from $\alpha$-iron, isolated iron atoms and mixtures thereof.

23. A process as set forth in claim 22 wherein said transition metal/nitrogen composition as determined from Mössbauer spectra comprises from about 15% to about 25% by weight $\alpha$-iron, and from about 10% to about 20% by weight isolated iron atoms.

24. A process as set forth in claim 12 wherein the atomic ratio of transition metal to nitrogen in said transition metal/nitrogen composition is from about 1:4 to about 3:1.

25. A process as set forth in claim 12 wherein said organic substrate comprises a tertiary amine which is oxidized to a secondary amine.

26. A process as set forth in claim 25 wherein said tertiary amine substrate corresponds to a compound of Formula I having the structure:

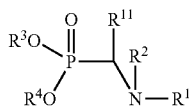

[Formula I]

wherein $R^1$ is selected from the group consisting of $R^5OC(O)CH_2$— and $R^5OCH_2CH_2$—, $R^2$ is selected from the group consisting of $R^5OC(O)CH_2$—, hydrocarbyl, substituted hydrocarbyl, acyl, —$CHR^6PO_3R^7R^8$, and —$CHR^9SO_3R^{10}$, $R^6$, $R^9$ and $R^{11}$ are selected from the group consisting of hydrogen, alkyl, halogen and —$NO_2$, and $R^3$, $R^4$, $R^5$, $R^7$, $R^8$ and $R^{10}$ are independently selected from the group consisting of hydrogen, hydrocarbyl, substituted hydrocarbyl and a metal ion.

27. A process as set forth in claim 26 wherein $R^1$ comprises $R^5OC(O)CH_2$—, $R^{11}$ is hydrogen, and $R^5$ is selected from hydrogen and an agronomically acceptable cation.

28. A process as set forth in claim 27 wherein $R^2$ is selected from the group consisting of $R^5OC(O)CH_2$—, acyl, hydrocarbyl and substituted hydrocarbyl.

29. A process as set forth in claim 25 wherein said tertiary amine substrate comprises N-(phosphonomethyl)iminodiacetic acid or a salt thereof.

30. A process as set forth in claim 29 wherein said catalyst functions to catalyze both the oxidation of said tertiary amine substrate and the further oxidation of formaldehyde and formic acid produced as by-products of the oxidation of said tertiary amine substrate.

31. A process for the oxidation of an organic substrate selected from the group consisting of carbohydrates, alcohols, aldehydes, tertiary amines, secondary amines and acids, wherein the alcohols are oxidized to aldehydes, ketones and/or acids, the aldehydes are oxidized to acids, the tertiary amines are oxidized to secondary amines, the secondary amines are oxidized to primary amines and the acids are oxidized to carbon dioxide and water, the process comprising contacting said substrate with an oxidizing agent in the presence of an oxidation catalyst, said oxidation catalyst comprising a modified particulate carbon support comprising a particulate carbon support having a transition metal/nitrogen composition thereon, said transition metal/nitrogen composition comprising an iron or cobalt nitride, an iron or cobalt nitride-carbide or combinations thereof, said catalyst comprising said transition metal/nitrogen composition in such proportion that the Fe, Co or the sum of (Fe+Co) of said transition metal/nitrogen composition constitutes at least about 0.1% by weight of said catalyst, and the nitrogen of said transition metal/nitrogen composition constitutes at least about 0.01% by weight of said catalyst.

32. A process as set forth in claim 31 wherein said transition metal/nitrogen composition is fixed to the modified carbon support.

33. A process as set forth in claim 31 wherein said transition metal/nitrogen composition comprises an active phase for the catalysis of a redox reaction.

34. A process as set forth in claim 31 wherein said transition metal/nitrogen composition comprises an iron or cobalt nitride.

35. A process as set forth in claim 31 wherein said transition metal/nitrogen composition constitutes at least about 0.2% by weight of said catalyst.

36. A process as set forth in claim 34 wherein said transition metal/nitrogen composition constitutes from about 0.4% to about 6% by weight of said catalyst.

37. A process as set forth in claim 31 wherein said catalyst comprises said transition metal/nitrogen composition in such proportion that the Fe, Co or the sum of (Fe+Co) of said transition metal/nitrogen composition constitutes from about 0.1% to about 10% by weight of said catalyst, and the nitrogen of said transition metal/nitrogen composition constitutes from about 0.01% to about 10% by weight of said catalyst.

38. A process as set forth in claim 37 wherein said catalyst comprises said transition metal/nitrogen composition in such proportion that the Fe, Co or the sum of (Fe+Co) of said transition metal/nitrogen composition constitutes from about 0.25% to about 7% by weight of said catalyst, and the nitrogen of said transition metal/nitrogen composition constitutes from about 0.1% to about 7% by weight of said catalyst.

39. A process as set forth in claim 38 wherein said catalyst comprises said transition metal/nitrogen composition in such proportion that the Fe, Co or the sum of (Fe+Co) of said transition metal/nitrogen composition constitutes from about 0.5% to about 5% by weight of said catalyst, and the nitrogen of said transition metal/nitrogen composition constitutes from about 1% to about 5% by weight of said catalyst.

40. A process as set forth in claim 37 wherein said catalyst comprises said transition metal/nitrogen composition in such proportion that the Fe, Co or the sum of (Fe+Co) of said transition metal/nitrogen composition constitutes from about 0.2% to about 3% by weight of said catalyst, and the nitrogen of said transition metal/nitrogen composition constitutes from about 0.2% to about 3% by weight of said catalyst.

41. A process as set forth in claim 37 wherein said particulate carbon support is porous and said transition metal/nitrogen composition is substantially evenly distributed throughout the carbon particle.

42. A process as set forth in claim 37 wherein said transition metal/nitrogen composition comprises an iron or cobalt nitride.

43. A process as set forth in claim 42 wherein said transition metal/nitrogen composition comprises $\xi$-$Fe_3N$.

44. A process as set forth in claim 43 wherein said transition metal/nitrogen composition further comprises an iron species selected from the group consisting of iron oxides, iron carbides, and metallic iron.

45. A process as set forth in claim 42 wherein said transition metal/nitrogen composition comprises an iron nitride and superparamagnetic iron.

46. A process as set forth in claim 45 wherein said transition metal/nitrogen composition as determined from Mössbauer spectra comprises from about 30% to about 70% by weight $\xi$-$Fe_3N$ and from about 5% to about 20% by weight superparamagnetic iron.

47. A process as set forth in claim 37 wherein said transition metal/nitrogen composition as determined from Mössbauer spectra further comprises an additional iron species selected from α-iron, isolated iron atoms and mixtures thereof.

48. A process as set forth in claim 47 wherein said transition metal/nitrogen composition as determined from Mössbauer spectra comprises from about 15% to about 25% by weight α-iron, and from about 10% to about 20% by weight isolated iron atoms.

49. A process as set forth in claim 37 wherein the atomic ratio of transition metal to nitrogen in said transition metal/nitrogen composition is from about 1:4 to about 3:1.

50. A process as set forth in claim 37 wherein said organic substrate comprises a tertiary amine which is oxidized to a secondary amine.

51. A process as set forth in claim 2 wherein said transition metal and said nitrogen of said transition metal/nitrogen composition are bound to said carbon support.

52. A process as set forth in claim 2 wherein said oxidizing agent is an oxygen-containing gas comprising molecular oxygen.

53. A process as set forth in claim 52 wherein said modified carbon support is effective for reduction of oxygen as characterized by an increased reduction current relative to an untreated carbon support under reference conditions wherein the catalyst serves as an electrode that is cycled in the range of +0.1 to +0.5 volts vs. an Ag/AgCl electrode in the cyclic voltammetric reduction of oxygen at 70° C. in an electrolytic medium consisting of 0.1M $H_3PO_4$.

54. A process as set forth in claim 8 wherein said particulate carbon support is in the form of granules.

55. A process as set forth in claim 8 wherein said particulate carbon support is in the form of a powder having a particle size distribution such that at least about 98% of the particles are from about 2 to about 200 μm in their largest dimension.

56. A process as set forth in claim 8 wherein said particulate carbon support comprises activated carbon.

57. A process as set forth in claim 8 wherein said particulate carbon support has a specific surface area as measured by the Brunauer-Emmett-Teller (BET) method of from about 500 to about 2,100 $m^2/g$.

58. A process as set forth in claim 8 wherein said particulate carbon support has a pore volume of from about 0.2 to about 2.0 ml/g.

59. A process as set forth in claim 9 wherein said transition metal/nitrogen composition constitutes from about 0.4% to about 15% by weight of said catalyst.

60. A process as set forth in claim 12 wherein the surface of the modified carbon support is substantially devoid of any discrete transition metal particles greater than about 5 μm in their largest dimension.

61. A process as set forth in claim 12 wherein said transition metal/nitrogen composition comprises cobalt nitride.

62. A process as set forth in claim 61 wherein said transition metal/nitrogen composition further comprises a cobalt species selected from the group consisting of cobalt oxides, cobalt carbides and metallic cobalt.

63. A process as set forth in claim 12 wherein the noble metal is at the surface of the modified carbon support in the form of metal particles.

64. A process as set forth in claim 63 wherein at least 90% of the noble metal particles at the surface of the modified carbon support are from about 1 to about 20 nm in their largest dimension.

65. A process as set forth in claim 64 wherein at least 80% of the noble metal particles at the surface of the modified carbon support are from about 1.5 to about 10 nm in their largest dimension.

66. A process as set forth in claim 12 wherein the oxidation catalyst further comprises at least one promoter metal associated with the noble metal at the surface of the modified carbon support, the promoter metal selected from the group consisting tin, cadmium, magnesium, manganese, nickel, aluminum, cobalt, bismuth, lead, titanium, antimony, selenium, iron, rhenium, zinc, cerium, zirconium, tellurium, germanium and combinations thereof.

67. A process as set forth in claim 66 wherein the promoter metal associated with the noble metal at the surface of the modified carbon support is more easily oxidized than the noble metal.

68. A process as set forth in claim 66 wherein the promoter metal associated with the noble metal at the surface of the modified carbon support is iron.

69. A process as set forth in claim 66 wherein the concentration of the promoter metal associated with the noble metal at the surface of the modified carbon support is from about 0.1% to about 2% by weight of the catalyst.

70. A process as set forth in claim 66 wherein noble metal atoms at the surface of the modified carbon support are alloyed with the promoter metal to form alloyed metal particles.

71. A process as set forth in claim 70 wherein substantially all of the noble metal atoms at the surface of the modified carbon support are alloyed with the promoter metal.

72. A process as set forth in claim 70 wherein at least 80% of the alloyed metal particles at the surface of the modified carbon support are from about 1 to about 20 nm in their largest dimension.

73. A process as set forth in claim 72 wherein at least 80% of the alloyed metal particles at the surface of the modified carbon support are from about 1.5 to about 7 nm in their largest dimension.

74. A process as set forth in claim 32 wherein said transition metal and said nitrogen of said transition metal/nitrogen composition are bound to said carbon support.

75. A process as set forth in claim 31 wherein said oxidizing agent is an oxygen-containing gas comprising molecular oxygen.

76. A process as set forth in claim 75 wherein said modified support is effective for reduction of oxygen as characterized by an increased reduction current relative to an untreated carbon support under reference conditions wherein the catalyst serves as an electrode that is cycled in the range of +0.1 to +0.5 volts vs. an Ag/AgCl electrode in the cyclic voltammetric reduction of oxygen at 70° C. in an electrolytic medium consisting of 0.1M $H_3PO_4$.

77. A process as set forth in claim 31 wherein said particulate carbon support is in the form of granules.

78. A process as set forth in claim 31 wherein said particulate carbon support is in the form of a powder having a particle size distribution such that at least about 98% of the particles are from about 2 to about 200 μm in their largest dimension.

79. A process as set forth in claim 31 wherein said particulate carbon support comprises activated carbon.

80. A process as set forth in claim 31 wherein said particulate carbon support has a specific surface area as measured by the Brunauer-Emmett-Teller (BET) method of from about 500 to about 2,100 $m^2/g$.

81. A process as set forth in claim 31 wherein said particulate carbon support has a pore volume of from about 0.2 to about 2.0 ml/g.

82. A process as set forth in claim 35 wherein said transition metal/nitrogen composition constitutes from about 0.4% to about 15% by weight of said catalyst.

83. A process as set forth in claim 37 wherein the surface of the modified carbon support is substantially devoid of any discrete transition metal particles greater than about 5 μm in their largest dimension.

84. A process as set forth in claim 37 wherein said transition metal/nitrogen composition comprises cobalt nitride.

85. A process as set forth in claim 84 wherein said transition metal/nitrogen composition further comprises a cobalt species selected from the group consisting of cobalt oxides, cobalt carbides and metallic cobalt.

86. A process as set forth in claim 50 wherein said tertiary amine substrate corresponds to a compound of Formula I having the structure:

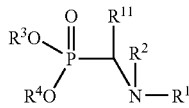

[Formula I]

wherein $R^1$ is selected from the group consisting of $R^5OC(O)CH_2$— and $R^5OCH_2CH_2$—, $R^2$ is selected from the group consisting of $R^5OC(O)CH_2$—, hydrocarbyl, substituted hydrocarbyl, acyl, —$CHR^6PO_3R^7R^8$, and —$CHR^9SO_3R^{10}$, $R^6$, $R^9$ and $R^{11}$ are selected from the group consisting of hydrogen, alkyl, halogen and —$NO_2$, and $R^3$, $R^4$, $R^5$, $R^7$, $R^8$ and $R^{10}$ are independently selected from the group consisting of hydrogen, hydrocarbyl, substituted hydrocarbyl and a metal ion.

87. A process as set forth in claim 86 wherein $R^1$ comprises $R^5OC(O)CH_2$—, $R^{11}$ is hydrogen, and $R^5$ is selected from hydrogen and an agronomically acceptable cation.

88. A process as set forth in claim 87 wherein $R^2$ is selected from the group consisting of $R^5OC(O)CH_2$—, acyl, hydrocarbyl and substituted hydrocarbyl.

89. A process as set forth in claim 50 wherein said tertiary amine substrate comprises N-(phosphonomethyl)iminodiacetic acid or a salt thereof.

90. A process as set forth in claim 89 wherein said catalyst functions to catalyze both the oxidation of said tertiary amine substrate and the further oxidation of formaldehyde and formic acid produced as by-products of the oxidation of said tertiary amine substrate.

91. A process as set forth in claim 52 wherein said active phase is effective for catalyzing the reduction of molecular oxygen.

92. A process as set forth in claim 75 wherein said active phase is effective for catalyzing the reduction of molecular oxygen.

* * * * *